US012018303B2

(12) United States Patent
Von Langermann et al.

(10) Patent No.: US 12,018,303 B2
(45) Date of Patent: Jun. 25, 2024

(54) METHOD FOR PREPARING AMINES FROM CARBONYL COMPOUNDS BY TRANSAMINASE REACTION UNDER SALT PRECIPITATION

(71) Applicants: ENZYMICALS AG, Greifswald (DE); UNIVERSITÄT ROSTOCK, Rostock (DE)

(72) Inventors: Jan Von Langermann, Rostock (DE); Dennis Hülsewede, Rostock (DE); Marco Cornelius, Potsdam (DE); Ulf Menyes, Neu Boltenhagen (DE); Philipp Süss, Greifswald (DE)

(73) Assignee: Enzymicals AG, Greifswald (DE)

( * ) Notice: Subject to any disclaimer, the term of this patent is extended or adjusted under 35 U.S.C. 154(b) by 672 days.

(21) Appl. No.: 16/764,476

(22) PCT Filed: Nov. 16, 2018

(86) PCT No.: PCT/EP2018/081517
§ 371 (c)(1),
(2) Date: May 15, 2020

(87) PCT Pub. No.: WO2019/096973
PCT Pub. Date: May 23, 2019

(65) Prior Publication Data

US 2022/0162654 A1 May 26, 2022
US 2023/0167472 A9 Jun. 1, 2023

(30) Foreign Application Priority Data

Nov. 17, 2017 (EP) .................................... 17202282

(51) Int. Cl.
*C12P 13/00* (2006.01)
*C07C 57/30* (2006.01)
*C07C 211/63* (2006.01)
*C12P 7/40* (2006.01)

(52) U.S. Cl.
CPC ............ *C12P 13/005* (2013.01); *C07C 57/30* (2013.01); *C07C 211/63* (2013.01); *C12P 7/40* (2013.01)

(58) Field of Classification Search
CPC ........... C12P 13/005; C12P 7/40; C12P 13/00; C12P 13/001; C07C 57/30; C07C 211/63; C12N 9/1096
USPC .......................................................... 562/491
See application file for complete search history.

(56) References Cited

U.S. PATENT DOCUMENTS 8,377,666 B2 2/2013 Haselbeck et al.
10,023,886 B2 7/2018 Schurmann et al.

FOREIGN PATENT DOCUMENTS

JP 2010537656 A 12/2010
JP 2013507145 A 3/2013
JP 2013530713 A 8/2013
WO 2011026556 A1 3/2011

OTHER PUBLICATIONS

Database UniParc [Online] Apr. 14, 2017 (Apr. 14, 2017), N.N.: "*Mycobacterium bacteremicum*", XP002780153, Database accession No. UPI0009F6A547.

Buque-Taboada et al: "In situ product recovery (ISPR) by crystallization: basic principles, design, and potential applications in whole-cell biocatalysis", Applied Microbiology and Biotechnology, vol. 71, 2006, pp. 1-12, XP019422047.

Heintz et al: "Development of in situ product removal strategies in biocatalysis applying scaled-down unit operations", Biotechnology and Bioengineering, vol. 114, Oct. 12, 2016 (Oct. 12, 2016), pp. 600-609, XP002780154.

Borner et al: "A process concept for high-purity production of amines by transaminase-catalyzed asymmetric synthesis: combining enzyme cascade and membrane-assisted ISPR", Organic Process Research & Development, vol. 19, 2015, pp. 793-799, XP055265098.

Hulsewede et al: "Development of an in situ-product crystallization (ISPC)-concept to shift the reaction equilibria of selected amine transaminase-catalyzed reactions", European Journal of Organic Chemistry 10.1002/EJOC.201800323, Mar. 2018 (Mar. 2018), pp. 1-5, XP002780145.

Hulsewede et al: "Application of in situ product crystallization and related techniques in biocatalytic processes", Chemistry—A European Journal, vol. 25, Nov. 5, 2018 (Nov. 5, 2018), pp. 1-15, XP002788836.

Von Langermann: "Equilibrium displacement by in situ-product crystallisation (ISPC) in transaminase-catalysed reactions", Amine Biocat 3.0, Manchester, Dec. 2017, Conference presentation, Dec. 2017 (Dec. 2017), pp. 1-3, XP002780155, Retrieved from the Internet: URL:https://aminebiocat3.com/wp-content/uploads/Amine_Biocat_3-0Agenda.pdf [retrieved on Apr. 17, 2018].

International Search Report and Written Opinion for International Patent Application No. PCT/EP2018/081517, dated Feb. 26, 2019, 14 pages.

*Primary Examiner* — Ana Z Muresan
(74) *Attorney, Agent, or Firm* — Armstrong Teasdale LLP

(57) ABSTRACT

Described herein is a method for preparing an amino salt compound, the method including: i) providing a carbonyl compound; ii) reacting the carbonyl compound provided according to (i) in the presence of a transaminase with ii-a) at least one primary amine; and ii-b) at least one carboxylic acid; thereby obtaining a mixture including an at least partially crystallized amino salt compound including a cation and a carboxylate anion based on the at least one carboxylic acid added according to (ii-b). Also described herein is an amino salt compound obtained or obtainable by the method and to the amino salt compound, and a composition including a) an amine of general formula (IIa); and b) at least one carboxylic acid of general formula (III).

11 Claims, 2 Drawing Sheets

Specification includes a Sequence Listing.

SEQUENCE LISTING

<160> NUMBER OF SEQ ID NOS: 7

<210> SEQ ID NO 1
<211> LENGTH: 323
<212> TYPE: PRT
<213> ORGANISM: Aspergillus fumigates

<400> SEQUENCE: 1

```
Met Ala Ser Met Asp Lys Val Phe Ser Gly Tyr Tyr Ala Arg Gln Lys
1               5                   10                  15

Leu Leu Glu Arg Ser Asp Asn Pro Phe Ser Lys Gly Ile Ala Tyr Val
            20                  25                  30

Glu Gly Lys Leu Val Leu Pro Ser Asp Ala Arg Ile Pro Leu Leu Asp
        35                  40                  45

Glu Gly Phe Met His Ser Asp Leu Thr Tyr Asp Val Ile Ser Val Trp
    50                  55                  60

Asp Gly Arg Phe Phe Arg Leu Asp Asp His Leu Gln Arg Ile Leu Glu
65                  70                  75                  80

Ser Cys Asp Lys Met Arg Leu Lys Phe Pro Leu Ala Leu Ser Ser Val
                85                  90                  95

Lys Asn Ile Leu Ala Glu Met Val Ala Lys Ser Gly Ile Arg Asp Ala
            100                 105                 110

Phe Val Glu Val Ile Val Thr Arg Gly Leu Thr Gly Val Arg Gly Ser
        115                 120                 125

Lys Pro Glu Asp Leu Tyr Asn Asn Asn Ile Tyr Leu Leu Val Leu Pro
    130                 135                 140

Tyr Ile Trp Val Met Ala Pro Glu Asn Gln Leu His Gly Gly Glu Ala
145                 150                 155                 160

Ile Ile Thr Arg Thr Val Arg Arg Thr Pro Pro Gly Ala Phe Asp Pro
                165                 170                 175

Thr Ile Lys Asn Leu Gln Trp Gly Asp Leu Thr Lys Gly Leu Phe Glu
            180                 185                 190

Ala Met Asp Arg Gly Ala Thr Tyr Pro Phe Leu Thr Asp Gly Asp Thr
        195                 200                 205

Asn Leu Thr Glu Gly Ser Gly Phe Asn Ile Val Leu Val Lys Asn Gly
    210                 215                 220

Ile Ile Tyr Thr Pro Asp Arg Gly Val Leu Arg Gly Ile Thr Arg Lys
225                 230                 235                 240

Ser Val Ile Asp Val Ala Arg Ala Asn Ser Ile Asp Ile Arg Leu Glu
                245                 250                 255

Val Val Pro Val Glu Gln Ala Tyr His Ser Asp Glu Ile Phe Met Cys
            260                 265                 270

Thr Thr Ala Gly Gly Ile Met Pro Ile Thr Leu Leu Asp Gly Gln Pro
        275                 280                 285

Val Asn Asp Gly Gln Val Gly Pro Ile Thr Lys Lys Ile Trp Asp Gly
    290                 295                 300

Tyr Trp Glu Met His Tyr Asn Pro Ala Tyr Ser Phe Pro Val Asp Tyr
305                 310                 315                 320

Gly Ser Gly
```

<210> SEQ ID NO 2
<211> LENGTH: 325
<212> TYPE: PRT
<213> ORGANISM: Gibberella zeae

<400> SEQUENCE: 2

```
Met Ser Thr Met Asp Lys Ile Phe Ala Gly His Ala Gln Arg Gln Ala
1               5                   10                  15

Thr Leu Val Ala Ser Asp Asn Ile Phe Ala Asn Gly Ile Ala Trp Ile
            20                  25                  30

Gln Gly Glu Leu Val Pro Leu Asn Glu Ala Arg Ile Pro Leu Met Asp
        35                  40                  45

Gln Gly Phe Met His Gly Asp Leu Thr Tyr Asp Val Pro Ala Val Trp
    50                  55                  60

Asp Gly Arg Phe Phe Arg Leu Asp Asp His Leu Asp Arg Leu Glu Ala
65                  70                  75                  80

Ser Val Lys Lys Met Arg Met Gln Phe Pro Ile Pro Arg Asp Glu Ile
                85                  90                  95

Arg Met Thr Leu Leu Asp Met Leu Ala Lys Ser Gly Ile Lys Asp Ala
            100                 105                 110

Phe Val Glu Leu Ile Val Thr Arg Gly Leu Lys Pro Val Arg Glu Ala
        115                 120                 125

Lys Pro Gly Glu Val Leu Asn Asn His Leu Tyr Leu Ile Val Gln Pro
    130                 135                 140

Tyr Val Trp Val Met Ser Pro Glu Ala Gln Tyr Val Gly Gly Asn Ala
145                 150                 155                 160

Val Ile Ala Arg Thr Val Arg Arg Ile Pro Pro Gly Ser Met Asp Pro
                165                 170                 175

Thr Ile Lys Asn Leu Gln Trp Ser Asp Phe Thr Arg Gly Met Phe Glu
            180                 185                 190

Ala Tyr Asp Arg Gly Ala Gln Tyr Pro Phe Leu Thr Asp Gly Asp Thr
        195                 200                 205

Asn Ile Thr Glu Gly Ser Gly Phe Asn Val Val Phe Val Lys Asn Asn
    210                 215                 220

Val Ile Tyr Thr Pro Asn Arg Gly Val Leu Gln Gly Ile Thr Arg Lys
225                 230                 235                 240

Ser Val Ile Asp Ala Ala Lys Trp Cys Gly His Glu Val Arg Val Glu
                245                 250                 255

Tyr Val Pro Val Glu Met Ala Tyr Glu Ala Asp Glu Ile Phe Met Cys
            260                 265                 270

Thr Thr Ala Gly Gly Ile Met Pro Ile Thr Thr Met Asp Gly Lys Pro
        275                 280                 285

Val Lys Asp Gly Lys Val Gly Pro Val Thr Lys Ala Ile Trp Asp Arg
    290                 295                 300

Tyr Trp Ala Met His Trp Glu Asp Glu Phe Ser Phe Lys Ile Asp Tyr
305                 310                 315                 320

Gln Lys Leu Lys Leu
                325
```

<210> SEQ ID NO 3
<211> LENGTH: 323
<212> TYPE: PRT
<213> ORGANISM: Neosartorya fischeri

<400> SEQUENCE: 3

```
Met Ala Ser Met Asp Lys Val Phe Ser Gly Tyr His Ala Arg Gln Lys
1               5                   10                  15

Leu Leu Glu Arg Ser Asp Asn Pro Phe Ser Lys Gly Ile Ala Tyr Val
            20                  25                  30

Glu Gly Lys Leu Val Leu Pro Ser Asp Ala Arg Ile Pro Leu Leu Asp
```

```
        35                  40                  45

Glu Gly Phe Met His Gly Asp Leu Thr Tyr Asp Val Thr Thr Val Trp
    50                  55                  60

Asp Gly Arg Phe Phe Arg Leu Asp Asp His Met Gln Arg Ile Leu Glu
65                  70                  75                  80

Ser Cys Asp Lys Met Arg Leu Lys Phe Pro Leu Ala Pro Ser Thr Val
                85                  90                  95

Lys Asn Ile Leu Ala Glu Met Val Ala Lys Ser Gly Ile Arg Asp Ala
            100                 105                 110

Phe Val Glu Val Ile Val Thr Arg Gly Leu Thr Gly Val Arg Gly Ser
        115                 120                 125

Lys Pro Glu Asp Leu Tyr Asn Asn Asn Ile Tyr Leu Leu Val Leu Pro
    130                 135                 140

Tyr Val Trp Val Met Ala Pro Glu Asn Gln Leu Leu Gly Gly Ser Ala
145                 150                 155                 160

Ile Ile Thr Arg Thr Val Arg Arg Thr Pro Pro Gly Ala Phe Asp Pro
                165                 170                 175

Thr Ile Lys Asn Leu Gln Trp Gly Asp Leu Thr Lys Gly Leu Phe Glu
            180                 185                 190

Ala Met Asp Arg Gly Ala Thr Tyr Pro Phe Leu Thr Asp Gly Asp Thr
        195                 200                 205

Asn Leu Thr Glu Gly Ser Gly Phe Asn Ile Val Leu Val Lys Asn Gly
    210                 215                 220

Ile Ile Tyr Thr Pro Asp Arg Gly Val Leu Arg Gly Ile Thr Arg Lys
225                 230                 235                 240

Ser Val Ile Asp Val Ala Arg Ala Asn Asn Ile Asp Ile Arg Leu Glu
                245                 250                 255

Val Val Pro Val Glu Gln Val Tyr His Ser Asp Glu Ile Phe Met Cys
            260                 265                 270

Thr Thr Ala Gly Gly Ile Met Pro Ile Thr Leu Leu Asp Gly Gln Pro
        275                 280                 285

Val Asn Asp Gly Gln Val Gly Pro Ile Thr Lys Lys Ile Trp Asp Gly
    290                 295                 300

Tyr Trp Glu Met His Tyr Asn Pro Ala Tyr Ser Phe Pro Val Asp Tyr
305                 310                 315                 320

Gly Ser Gly


<210> SEQ ID NO 4
<211> LENGTH: 326
<212> TYPE: PRT
<213> ORGANISM: Aspergillus oryzae

<400> SEQUENCE: 4

Met Thr Ser Met Asn Lys Val Phe Ser Gly Tyr Tyr Glu Arg Lys Ala
1               5                   10                  15

Arg Leu Asp Asn Ser Asp Asn Arg Phe Ala Lys Gly Ile Ala Tyr Val
            20                  25                  30

Gln Gly Ser Phe Val Pro Leu Ala Asp Ala Arg Val Pro Leu Leu Asp
        35                  40                  45

Glu Gly Phe Met His Ser Asp Leu Thr Tyr Asp Val Pro Ser Val Trp
    50                  55                  60

Asp Gly Arg Phe Phe Arg Leu Asp Asp His Leu Ser Arg Leu Glu Asp
65                  70                  75                  80

Ser Cys Glu Lys Met Arg Leu Lys Ile Pro Leu Ser Arg Asp Glu Val
```

```
                85                  90                  95

Lys Gln Thr Leu Arg Glu Met Val Ala Lys Ser Gly Ile Glu Asp Ala
            100                 105                 110

Phe Val Glu Leu Ile Val Thr Arg Gly Leu Lys Gly Val Arg Gly Asn
        115                 120                 125

Lys Pro Glu Asp Leu Phe Asp Asn His Leu Tyr Leu Ile Val Met Pro
    130                 135                 140

Tyr Val Trp Val Met Glu Pro Ala Ile Gln His Thr Gly Gly Thr Ala
145                 150                 155                 160

Ile Ile Ala Arg Thr Val Arg Arg Thr Pro Pro Gly Ala Phe Asp Pro
                165                 170                 175

Thr Ile Lys Asn Leu Gln Trp Gly Asp Leu Thr Arg Gly Leu Phe Glu
            180                 185                 190

Ala Ala Asp Arg Gly Ala Asp Tyr Pro Phe Leu Ser Asp Gly Asp Thr
        195                 200                 205

Asn Leu Thr Glu Gly Ser Gly Phe Asn Ile Val Leu Val Lys Asp Gly
    210                 215                 220

Ile Ile Tyr Thr Pro Asp Arg Gly Val Leu Glu Gly Ile Thr Arg Lys
225                 230                 235                 240

Ser Val Phe Asp Ile Ala Gln Val Lys Asn Ile Glu Val Arg Val Gln
                245                 250                 255

Val Val Pro Leu Glu His Ala Tyr His Ala Asp Glu Ile Phe Met Cys
            260                 265                 270

Thr Thr Ala Gly Gly Ile Met Pro Ile Thr Lys Leu Asp Gly Lys Pro
        275                 280                 285

Ile Arg Asn Gly Glu Val Gly Pro Leu Thr Thr Lys Ile Trp Asp Glu
    290                 295                 300

Tyr Trp Ala Met His Tyr Asp Pro Lys Tyr Ser Ser Ala Ile Asp Tyr
305                 310                 315                 320

Arg Gly His Glu Gly Asn
                325


<210> SEQ ID NO 5
<211> LENGTH: 325
<212> TYPE: PRT
<213> ORGANISM: Aspergillus terreus

<400> SEQUENCE: 5

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125
```

```
Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
            180                 185                 190

Glu Ala Ala Asp Arg Gly Ala Thr Tyr Pro Phe Leu Thr Asp Gly Asp
        195                 200                 205

Ala His Leu Thr Glu Gly Ser Gly Phe Asn Ile Val Leu Val Lys Asp
    210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

Glu Phe Val Pro Val Glu Leu Ala Tyr Arg Cys Asp Glu Ile Phe Met
            260                 265                 270

Cys Thr Thr Ala Gly Gly Ile Met Pro Ile Thr Thr Leu Asp Gly Met
        275                 280                 285

Pro Val Asn Gly Gly Gln Ile Gly Pro Ile Thr Lys Lys Ile Trp Asp
    290                 295                 300

Gly Tyr Trp Ala Met His Tyr Asp Ala Ala Tyr Ser Phe Glu Ile Asp
305                 310                 315                 320

Tyr Asn Glu Arg Asn
                325


<210> SEQ ID NO 6
<211> LENGTH: 339
<212> TYPE: PRT
<213> ORGANISM: Mycobacterium vanbaalenii

<400> SEQUENCE: 6

Met Thr Thr Leu Thr Asn Ala Gly Thr Ser Asn Leu Val Ala Val Glu
1               5                   10                  15

Pro Gly Ala Ile Arg Glu Asp Thr Pro Ala Gly Ser Val Ile Gln Tyr
            20                  25                  30

Ser Asp Tyr Glu Leu Asp Gln Ser Ser Pro Phe Ala Gly Gly Val Ala
        35                  40                  45

Trp Ile Glu Gly Glu Phe Val Pro Ala Glu Asp Ala Arg Ile Ser Ile
    50                  55                  60

Phe Asp Thr Gly Phe Gly His Ser Asp Leu Thr Tyr Thr Val Ala His
65                  70                  75                  80

Val Trp His Gly Asn Ile Phe Arg Leu Gly Asp His Leu Asp Arg Leu
                85                  90                  95

Leu Asp Gly Ala Arg Lys Leu Arg Leu Asp Ala Gly Tyr Thr Lys Asp
            100                 105                 110

Glu Leu Ala Asp Ile Thr Lys Gln Cys Val Ser Met Ser Gln Leu Arg
        115                 120                 125

Glu Ser Phe Val Asn Leu Thr Val Thr Arg Gly Tyr Gly Lys Arg Arg
    130                 135                 140

Gly Glu Lys Asp Leu Ser Lys Leu Thr His Gln Val Tyr Ile Tyr Ala
145                 150                 155                 160

Ile Pro Tyr Leu Trp Ala Phe Pro Pro Ala Glu Gln Ile Phe Gly Thr
                165                 170                 175
```

```
Thr Ala Ile Val Pro Arg His Val Arg Arg Ala Gly Arg Asn Thr Val
            180                 185                 190

Asp Pro Thr Ile Lys Asn Tyr Gln Trp Gly Asp Leu Thr Ala Ala Ser
        195                 200                 205

Phe Glu Ala Lys Asp Arg Gly Ala Arg Thr Ala Ile Leu Leu Asp Ser
    210                 215                 220

Asp Asn Cys Val Ala Glu Gly Pro Gly Phe Asn Val Cys Ile Val Lys
225                 230                 235                 240

Asp Gly Lys Leu Ala Ser Pro Ser Arg Asn Ala Leu Pro Gly Ile Thr
                245                 250                 255

Arg Lys Thr Val Phe Glu Leu Ala Asp Gln Met Gly Ile Glu Ala Thr
            260                 265                 270

Leu Arg Asp Val Thr Ser His Glu Leu Tyr Asp Ala Asp Glu Leu Met
        275                 280                 285

Ala Val Thr Thr Ala Gly Gly Val Thr Pro Ile Asn Ser Leu Asp Gly
    290                 295                 300

Glu Ala Ile Gly Asn Gly Glu Pro Gly Pro Met Thr Val Ala Ile Arg
305                 310                 315                 320

Asp Arg Phe Trp Ala Leu Met Asp Glu Pro Gly Pro Leu Ile Glu Ala
                325                 330                 335

Ile Glu Tyr
```

<210> SEQ ID NO 7
<211> LENGTH: 464
<212> TYPE: PRT
<213> ORGANISM: Silicibacter pomeroyi

<400> SEQUENCE: 7

```
Met Ala Thr Ile Thr Asn His Met Pro Thr Ala Glu Leu Gln Ala Leu
1               5                   10                  15

Asp Ala Ala His His Leu His Pro Phe Ser Ala Asn Asn Ala Leu Gly
            20                  25                  30

Glu Glu Gly Thr Arg Val Ile Thr Arg Ala Arg Gly Val Trp Leu Asn
        35                  40                  45

Asp Ser Glu Gly Glu Glu Ile Leu Asp Ala Met Ala Gly Leu Trp Cys
    50                  55                  60

Val Asn Ile Gly Tyr Gly Arg Asp Glu Leu Ala Glu Val Ala Ala Arg
65                  70                  75                  80

Gln Met Arg Glu Leu Pro Tyr Tyr Asn Thr Phe Phe Lys Thr Thr His
                85                  90                  95

Val Pro Ala Ile Ala Leu Ala Gln Lys Leu Ala Glu Leu Ala Pro Gly
            100                 105                 110

Asp Leu Asn His Val Phe Phe Ala Gly Gly Gly Ser Glu Ala Asn Asp
        115                 120                 125

Thr Asn Ile Arg Met Val Arg Thr Tyr Trp Gln Asn Lys Gly Gln Pro
    130                 135                 140

Glu Lys Thr Val Ile Ile Ser Arg Lys Asn Ala Tyr His Gly Ser Thr
145                 150                 155                 160

Val Ala Ser Ser Ala Leu Gly Gly Met Ala Gly Met His Ala Gln Ser
                165                 170                 175

Gly Leu Ile Pro Asp Val His His Ile Asn Gln Pro Asn Trp Trp Ala
            180                 185                 190

Glu Gly Gly Asp Met Asp Pro Glu Glu Phe Gly Leu Ala Arg Ala Arg
        195                 200                 205
```

-continued

```
Glu Leu Glu Glu Ala Ile Leu Glu Leu Gly Glu Asn Arg Val Ala Ala
    210                 215                 220

Phe Ile Ala Glu Pro Val Gln Gly Ala Gly Gly Val Ile Val Ala Pro
225                 230                 235                 240

Asp Ser Tyr Trp Pro Glu Ile Gln Arg Ile Cys Asp Lys Tyr Asp Ile
                245                 250                 255

Leu Leu Ile Ala Asp Glu Val Ile Cys Gly Phe Gly Arg Thr Gly Asn
            260                 265                 270

Trp Phe Gly Thr Gln Thr Met Gly Ile Arg Pro His Ile Met Thr Ile
        275                 280                 285

Ala Lys Gly Leu Ser Ser Gly Tyr Ala Pro Ile Gly Gly Ser Ile Val
    290                 295                 300

Cys Asp Glu Val Ala His Val Ile Gly Lys Asp Glu Phe Asn His Gly
305                 310                 315                 320

Tyr Thr Tyr Ser Gly His Pro Val Ala Ala Ala Val Ala Leu Glu Asn
                325                 330                 335

Leu Arg Ile Leu Glu Glu Glu Asn Ile Leu Asp His Val Arg Asn Val
            340                 345                 350

Ala Ala Pro Tyr Leu Lys Glu Lys Trp Glu Ala Leu Thr Asp His Pro
        355                 360                 365

Leu Val Gly Glu Ala Lys Ile Val Gly Met Met Ala Ser Ile Ala Leu
    370                 375                 380

Thr Pro Asn Lys Ala Ser Arg Ala Lys Phe Ala Ser Glu Pro Gly Thr
385                 390                 395                 400

Ile Gly Tyr Ile Cys Arg Glu Arg Cys Phe Ala Asn Asn Leu Ile Met
                405                 410                 415

Arg His Val Gly Asp Arg Met Ile Ile Ser Pro Pro Leu Val Ile Thr
            420                 425                 430

Pro Ala Glu Ile Asp Glu Met Phe Val Arg Ile Arg Lys Ser Leu Asp
        435                 440                 445

Glu Ala Gln Ala Glu Ile Glu Lys Gln Gly Leu Met Lys Ser Ala Ala
    450                 455                 460
```

METHOD FOR PREPARING AMINES FROM CARBONYL COMPOUNDS BY TRANSAMINASE REACTION UNDER SALT PRECIPITATION

CROSS-REFERENCE TO RELATED APPLICATIONS

This application is a national stage application of International Patent Application No. PCT/EP2018/081517, filed Nov. 16, 2018, which claims the benefit of priority to European Patent Application No. 17202282.4, filed Nov. 17, 2017, each of which is incorporated by reference herein in its entirety.

FIELD OF THE INVENTION

The present invention relates to a method for preparing an amino salt compound comprising: i) providing a carbonyl compound; ii) reacting the carbonyl compound provided according to (i) in the presence of a transaminase with ii-a) at least one primary amine; and ii-b) at least one carboxylic acid; thereby obtaining a mixture comprising an at least partially crystallized amino salt compound comprising an amino cation and a carboxylate anion based on the at least one carboxylic acid added according to (ii-b).

BACKGROUND

Biotransformations became over the past decades a powerful technique for the synthesis of valuable compounds on laboratory and industrial scale. Herein pyridoxal 5'-phosphate (PLP)-dependent transaminases (TAs) and especially amine transaminases (ATAs) have gained in recent years a significant impact in the synthesis of optically pure amines, which are valuable building blocks for various agrochemicals and active pharmaceutical ingredients, e.g. sitagliptin. These enzymes basically catalyze the deamination of a primary amine (amine donor) with a simultaneous amination of an aldehyde or ketone (amine acceptor). The transamination-reaction can be carried out as a kinetic resolution of a racemic amine or an asymmetric synthesis from the respective prochiral ketone. Due to a maximum yield of 100% the asymmetric synthesis is in theory preferred, especially if a catalyst with high enantioselectivity is used. Unfortunately thermodynamic limitations and certain product inhibitions tend to limit the applicability of transaminases in asymmetric synthesis, which needs to be overcome for synthetic purposes. Aside using an uneconomic excess of the amine donor, complex (co-)product removal techniques are currently considered, e.g. enzymatic cascades, membrane processes and non-catalytic side reactions. Such techniques unfortunately always increase (in general) overall complexity of the biocatalytic reaction systems, require additional or tailor-made co-substrates and generate further by-products.

SUMMARY

The object of the present invention was therefore the provision of a method for the preparation of a desired product amine via biotransformation, especially using a transaminase, which overcomes the above-mentioned drawbacks.

The object was solved by a method for preparing an amino salt compound comprising:

i) providing a carbonyl compound of general formula (I)

(I), wherein $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero) aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; or $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol;

ii) reacting the carbonyl compound provided according to (i) in the presence of a transaminase with ii-a) at least one primary amine; and ii-b) at least one carboxylic acid;

thereby obtaining a mixture comprising an at least partially crystallized amino salt compound comprising a cation of general formula (II)

(II), wherein $R^1$ and $R^2$ are as defined for general formula (I) and a carboxylate anion based on the at least one carboxylic acid added according to (ii-b).

The expression "amino salt compound" comprises cation and anion as described above. The amino salt compound can be present as pure salt compound (unsolvated, anhydrated) or as solvate or hydrate or mixture thereof, wherein hydrate includes hemihydrate, monohydrate and polyhydrate and solvate includes hemisolvate, monosolvate and polysolvate.

"At least partially crystallized" means that at least 50%, preferably at least 60%, more preferably at least 70%, more preferably at least 80%, more preferably at least 90% of the amine salt compound precipitate in crystalline form.

The wording "hetero" means that heteroatom(s) are present, which are selected from the group consisting of nitrogen atom, sulphur atom and oxygen atom, if not otherwise indicated. The heteroatom(s) is/are present as members of the respective chain or ring structure.

The residues $R^{1a, 2a}$ are as defined above. It has to be noted that neither $R^{1a}$ nor $R^{2a}$ is a substituent which comprises a charge, i.e., substituents having a charge are excluded as $R^{1a}$ and as $R^{2a}$. For example, $R^{1a}$ and also $R^{2a}$ are no carboxyl/carboxylate, no phosphate, no sulfonate.

In a preferred embodiment, the combination of $R^1$, $R^{1a}$ being a perfluorinated alkyl is excluded. The same applies for $R^2$ and $R^{2a}$, i.e. the combination of $R^2$ and $R^{2a}$ being a perfluorinated alkyl is excluded as well. In other words, neither the combination of $R^1$ and $R^{1a}$ nor the combination of $R^2$ and $R^{2a}$ is a perfluorinated alkyl.

Regarding the embodiment wherein $R^1$ and $R^2$ together form a C3-C10-cycloalkyl or a C3-C10-cycloalkenyl, the number of C atoms indicated includes the carbonyl C atom situated between $R^1$ and $R^2$.

DETAILED DESCRIPTION

Figure 1:
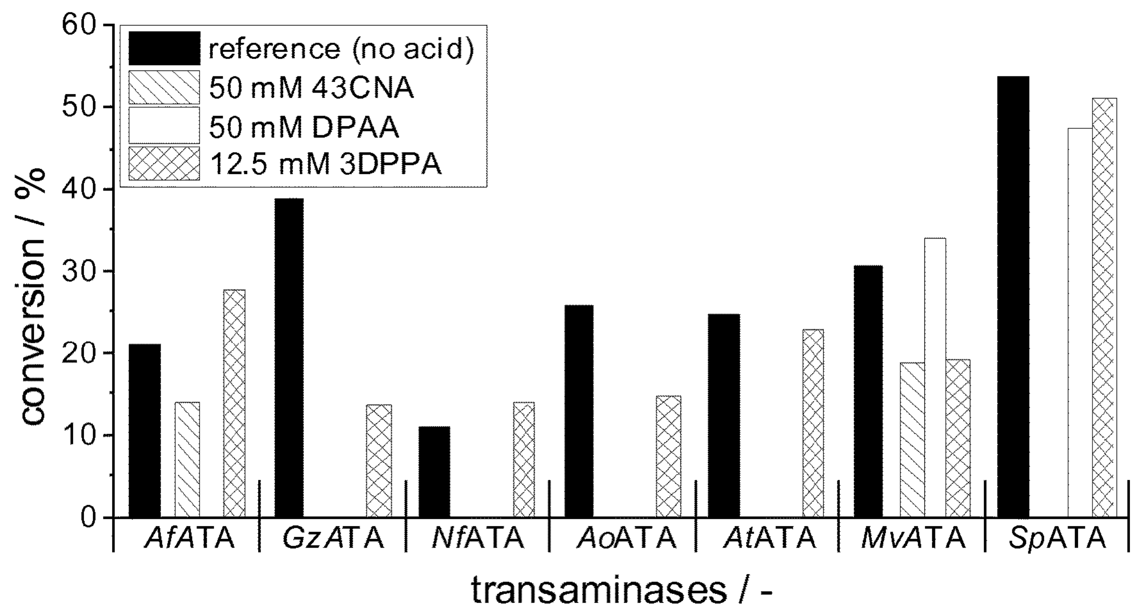
FIG. 1 Effects of 43CNA, DPAA and 3DPPA on selected amine transaminases; Conditions: 200 mM phosphate buffer pH 7.5, 10 mM acetophenone 1, 500 mM (43CNA and DPAA) or 250 mM (3DDPA) isopropylamine, 5 mg·mL$^{-1}$ lyophilized cell extract, 30° C., 22 h; the obtained concentrations of 2 were intentionally held below the solubility limit of product salt 6 to prevent an undesired in situ-product crystallization; 43CNA was chosen as a representative of the identified benzoic acid derivatives.

With this method as described above, the inventors now present a crystallization-based approach for the direct removal of the desired product amine from a transaminase-catalyzed reaction. Scheme 1 shows the method based on the exemplarily product amine 1-phenylethylamine. The product amine 2 is herein selectively crystallized from solution as a barely soluble amine salt 6, while all other reactants, especially the applied donor amine (isopropyl amine, 3), remains in solution. This in situ-product crystallization (ISPC) continuously removes the desired product amine from solution and thus yields an equilibrium displacement towards the products. The counter ion (here shown as a carboxylate) is added directly to the reaction solution and can be isolated for reuse from the formed solid salt. A stoichiometric use of the carboxylate in comparison to the applied amines is not required (see below).

Scheme 1: Combination of an in situ-product crystallization (ISPC) with a transaminase-catalyzed reaction to yield a barely soluble 1-phenylethylamine salt; shown protonation of reactants are based on an aqueous solution at pH 7.5; TA = transaminase, PLP = pyridoxal 5'-phosphate, R = exemplary residue representing a suitable carbon containing residue.

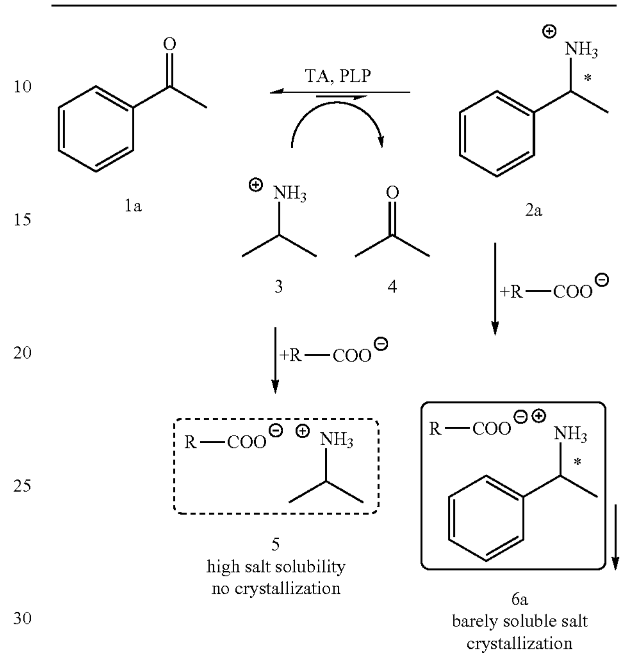

First, the main requirement of this concept is the choice of a specific counter ion, i.e. a specific carboxylic acid, which generates a barely soluble salt with the target amine for its crystallization, while the donor amine salt is not crystallized. Unfortunately, most commonly used amine salts, especially amine halide salts, show very high solubilities in aqueous solutions and thus are not applicable for such an ISPC concept. Thus, a preferred embodiment of the method is that the amino salt compound obtained according to (ii) has a solubility in water at pH 7 which is smaller than the solubility in water of the at least one primary amine added according to (ii-a). A further preferred embodiment of the method is that the amino salt compound obtained according to (ii) has a solubility in water at pH 7≤30 mmol/l, preferably ≤25 mmol/l, more preferably ≤10 mmol/l.

According to a preferred embodiment, the solubility difference (delta$_{Sol.}$) between the solubility of the salt of the primary amine and the solubility of the amino salt compound is at least 10 mmol/l. As explained above, the solubility of the salt of the primary amine (sol.$_{primary\ amine\ salt}$) is higher than the solubility of the amino salt compound (sol.$_{amino\ salt\ compound}$), i.e.:

$$sol._{primary\ amine\ salt} > sol._{amino\ salt\ compound}.$$

Second, the used transaminase has to tolerate the required concentration of the chosen compound. Third, the formed salt has to be stable under process conditions and should be easily recovered from the reaction mixture.

Carboxylic Acid

According to step (ii), the carbonyl compound provided according to (i) is reacted in the presence of a transaminase with ii-a) at least one primary amine; and ii-b) at least one carboxylic acid.

Regarding the carboxylic acid to be used for (ii-b), commercially readily available aliphatic, aromatic and heteroaromatic carboxylic acids (R—COOH) were selected and screened as their respective carboxylate salts towards common amines from a transaminase-catalyzed reaction. 1-phenylethylamine and substituted derivatives 2a-f thereof served as model product amines and were compared with typical donor amines such as isopropylamine 3, racemic 2-butylamine, DL-alanine and L-alanine (see Example section for further details). Here the salt of the product amine needs to exhibit a significant lower solubility then its donor amine salt counterpart since the donor amine is still applied with an excess.

Preferably, the at least one carboxylic acid according to (ii-b) is used in its protonated form or in deprotonated form with a suitable counter cation. The above-described straight-forward screening approach resulted in the finding, that the at least one carboxylic acid according to (ii-b) is preferably a carboxylic acid of general formula (III)

(III), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group; and the residue $R^5$ is hydrogen atom or methyl or absent if $R^3$ and $R^4$ together form a phenyl ring. The straight-forward screening approach especially resulted in two benzylbenzene-based acids and three benzoic acid derivatives that matched the above mentioned criteria (as the respective carboxylate ions at pH 7.5) (Scheme 2).

Scheme 2
Potential carboxylic acids and the abbreviations used for an in situ product crystallization of amines from a transaminase-catalyzed reaction.

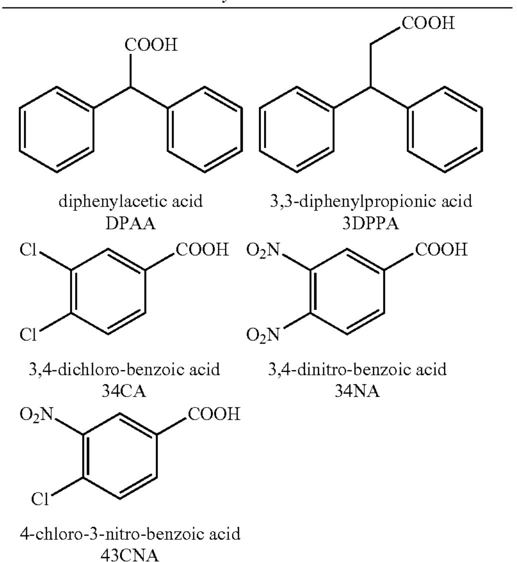

In addition, 2,2-diphenylpropionic acid (2DPPA) was identified as suitable carboxylic acid. Thus, a preferred embodiment of the method relates to the at least one carboxylic acid according to (ii-b) being a carboxylic acid selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA). More preferably, the at least one carboxylic acid according to (ii-b) is selected from the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA.

Carbonyl Compound

According to step (i), a carbonyl compound of general formula (I) is provided. Preferably, $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

More preferably, the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

According to a preferred embodiment of the method, the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20- aryl, C6-C20-alkylaryl, C6-C20-arylalkyl, C2-C20-heteroalkyl, C3-C20-cyclic heteroalkyl, wherein the hetero atom(s) is/are selected from oxygen, sulfur and nitrogen wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy. According to a further preferred embodiment of the method, the residue $R^1$ is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, C5-C20-cycloalkinyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy. According to a more preferred embodiment of the method, the residue $R^1$ is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, iso-propyl, cyclohexyl and phenyl, wherein phenyl has at least one substituent $R^{1a}$ selected from the group consisting of hydrogen atom, halogen atom, preferably fluoro or chloro, and methoxy, preferably meta- or para-methoxy.

For $R^1$ being branched or unbranched C2-C20-alkyl or branched or unbranched C2-C20-alkenyl, a preferred embodiment relates to $R^1$ being branched or unbranched C4-C20-alkyl or branched or unbranched C4-C20-alkenyl.

According to a preferred embodiment of the method, the residue $R^2$ is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy. According to a further preferred embodiment of the method, the residue $R^2$ is selected from the group of branched or unbranched C1-C3-alkyl, $R^2$ being preferably methyl.

Transaminase

According to step (ii), the carbonyl compound provided according to (i) is reacted in the presence of a transaminase. Preferably, the transaminase according to (ii) is selected from the group of transaminases, preferably from the group of amine transaminases, more preferably selected from the group consisting of amine transaminase from *Aspergillus* fumigates (AfATA) according to SEQ ID NO 1, amine transaminase from *Gibberella zeae* (GzATA) according to SEQ ID NO 2, amine transaminase from *Neosartorya fischeri* (NfATA) according to SEQ ID NO 3, amine transaminase from *Aspergillus oryzae* (AoATA) according to SEQ ID NO 4, amine transaminase from *Aspergillus terreus* (AtATA) according to SEQ ID NO 5, amine transaminase from *Mycobacterium vanbaalenii* (MvATA) according to SEQ ID NO 6, amine transaminase from *Silicibacter pomeroyi* (SpATA) according to SEQ ID NO 7 and a homologue enzyme having sequence identity of at least 65% with any one of SEQ ID NO 1 to 7 and having the same function as the amine transaminase of SEQ ID NO 1 to 7, more preferably selected from the group consisting of the amine transaminase from *Mycobacterium vanbaalenii* (MvATA) according to SEQ ID NO 6, the amine transaminase from *Silicibacter pomeroyi* (SpATA) according to SEQ ID NO 7 and a homologue enzyme having sequence identity of at least 65% with any one of SEQ ID NO 6 or 7 and having the same function as the amine transaminase of SEQ ID NO 6 or 7. Table 1 shows an overview of the preferred amine transaminases:

TABLE 1

Amine transaminases of SEQ ID Nos 1 to 7

| Name | Abbreviation | SEQ ID NO. | NCBI* accession no. | GenBank* accession no. |
|---|---|---|---|---|
| amine transaminase from Aspergillus fumigates | AfATA | 1 | XP_748821.1 | |
| amine transaminase from Gibberella zeae | GzATA | 2 | XP_011317603.1 | |
| amine transaminase from Neosartorya fischeri | NfATA | 3 | XP_001261640.1 | |
| amine transaminase from Aspergillus oryzae | AoATA | 4 | | BAE56564.1 |
| amine transaminase from Aspergillus terreus | AtATA | 5 | XP_001209325.1 | |
| amine transaminase from Mycobacterium vanbaalenii | MvATA | 6 | WP_083062280.1 | |
| amine transaminase from Silicibacter pomeroyi | SpATA | 7 | WP_011049154.1 | |

*Databank of the National Center for Biotechnology Information (https://www.ncbi.nlm.nih.gov/), status: Oct. 24, 2017

The expression "having the same function as the amine transaminase of any one of SEQ ID NO. 1 to 7" means that the homologue enzyme catalyzes an amine transaminase reaction at least with an effectivity of 90% as the transaminase of any one of SEQ ID NO. 1 to 7. Preferably, the homologue enzyme has a sequence identity of at least 75%, preferably at least 85%, more preferably at least 90%, more preferably at least 95%, more preferably at least 98%, more preferably at least 99%, with any one of SEQ ID NO 1 to 7 and has the same function as the amine transaminase of SEQ ID NO 1 to 7.

Primary Amine

According to step (ii), the carbonyl compound provided according to (i) is reacted in the presence of a transaminase with ii-a) at least one primary amine; and ii-b) at least one carboxylic acid. Preferably, the at least one primary amine according to (ii-a) is used in non-protonated form or in protonated form with a suitable counter anion.

According to a preferred embodiment of the method, the at least one primary amine according to (ii-a) is selected from the group of mono- and diamines having one to 10 carbon atoms, preferably from the group consisting of 1,5-diamino-pentane (cadaverine), alanine, 2-amino-butane (sec-butylamine) and 2-amino-propane, and is preferably 2-amino-propane (iso-propylamine) in its non-protonated or protonated form, wherein the protonated form is present in combination with a suitable anion.

According to a more preferred embodiment of the method, the at least one primary amine according to (ii-a) and the at least one carboxylic acid according to (ii-b) are used as one or more salt(s) comprising the protonated form of the at least one primary amine and the deprotonated form of the at least one carboxylic acid, preferably as one salt comprising the protonated form of the at least one primary amine and the deprotonated form of the at least one carboxylic acid, more preferably as isopropyl ammonium 3,3-diphenylpropionate.

Amino Salt Compound

According to step (ii), an amino salt compound is obtained. Preferably, the amino salt compound obtained according to (ii) comprises a cation of general formula (II)

(II), wherein $R^1$ and $R^2$ are as defined for general formula (I), and an anion based on the at least one carboxylic acid, which is preferably an anion of general formula (IIIa)

(IIIa), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; wherein the anion of general formula (IIIa) is preferably selected from the group consisting of diphenylacetate, 2,2-diphenylpropionate, 3,3-diphenylpropioniate, 3,4-dichloro-benzoate, 3,4-dinitro-benzoate and 4-chloro-3-nitro-benzoate, more preferably form the group consisting of diphenylacetate, 2,2-diphenylpropionate, 3,3-diphenylpropioniate, more preferably 2,2-diphenylpropionate or 3,3-diphenylpropionate, more preferably 3,3-diphenylpropionate.

Further Reaction Conditions

According to a preferred embodiment of the method, the reaction according to (ii) is carried out in an aqueous solution, which preferably comprises at least 80 weight-%, more preferably at least 90 weight-%, more preferably at least 95 weight-%, more preferably at least 98 weight-%, water, based on the overall weight of the aqueous solution. The aqueous solution preferably comprises a buffer, preferably selected from the group of tris(hydroxymethyl)aminomethane buffer (TRIS buffer), 3-(N-morpholino)propanesulfonic acid buffer (MOPS buffer), N,N-Bis(2-hydroxyethyl)-2-aminoethanesulfonic acid buffer (BES buffer), N-(tris(hydroxymethyl)methyl)-glycine buffer (Tricine buffer), Carbonate buffer, N-cyclohexyl-2-aminoethanesulfonic acid buffer (CHES buffer), 4-(2-hydroxyethyl)-1-piperazineethanesulfonic acid buffer (HEPES buffer) and phosphate buffer, more preferably at least a phosphate buffer.

According to further a preferred embodiment of the method, the reaction according to (ii) is carried out at a pH value in the range of 6.0 to 9.5, more preferably in the range of from 6.5 to 9.0, more preferably in the range of from 7.0 to 8.0. According to a further preferred embodiment of the method, the reaction according to (ii) is carried out for a time period of at least one hour, more preferably for a time in the range of from 1 to 1,000 hours, more preferably in the range of from 5 to 500 hours, more preferably in the range of from 10 to 200 hours. According to a further preferred embodiment of the method, the reaction according to (ii) is carried out at a temperature in the range of from 10 to 50° C., more preferably in the range of from 15 to 45° C., more preferably in the range of from 20 to 40° C., more preferably in the range of from 25 to 35° C.

According to another preferred embodiment of the method, for the at least one carboxylic acid being a carboxylic acid according to general formula (III), wherein the residues $R^3$ and $R^4$ together form a phenyl ring, preferably a carboxylic acid selected from the group consisting of 3,4-dichloro-benzoic acid (34CA), 3,4-dinitro-benzoic acid (34NA) and 4-chloro-3-nitro-benzoic acid (43CNA), the concentration of the at least one carboxylic acid is kept in the range of from 0.001 to 50 mM, preferably in the range of from 1 to 45 mM, more preferably in the range of from 5 to 40 mM during step (ii). According to another preferred embodiment of the method, for the at least one carboxylic acid being a carboxylic acid according to general formula (III), wherein the residues $R^3$ and $R^4$ are each a phenyl ring, preferably a carboxylic acid selected from the group consisting of diphenylacetic acid (DPAA), 2,2-diphenylpropionic acid (2DPPA) and 3,3-diphenylpropionic acid (3DPPA), the concentration of the at least one carboxylic acid is ≤50 mM during step (ii).

Further Reaction Steps

As described above, the method comprises reaction steps (i) and (ii). According to a preferred embodiment, the method further comprises:

iii) separating the at least partially crystallized amine salt compound obtained according to (ii) from the mixture thereby obtaining the crystallized amine salt compound.

Preferably, separating the crystallized amine salt compound according to (iii) from the mixture is done by sedimentation, centrifugation or filtration, preferably by filtration.

According to a further preferred embodiment, the method further comprises, preferably in addition to (i), (ii) and (iii):

(iv) optionally washing the separated crystallized amino salt compound obtained according to (iii), preferably with water or an organic solvent or a mixture thereof, more preferably with water or methyl tert-butyl ether or a mixture thereof, thereby obtaining a washed crystallized amino salt compound;

(v) dissolving the crystallized amino salt compound obtained according to (iii) or optionally the washed crystallized amino salt compound obtained according to (iv) in an aqueous solution having a pH value in the range of from 10 to 14 comprising at least one base, preferably a base comprising a hydroxide ion, thereby obtaining an aqueous solution comprising an amine of general formula (IIa)

(IIa), wherein $R^1$ and $R^2$ are as defined for general formula (I);

(vi) extracting the aqueous solution obtained according to (v) at least once with a water immiscible organic solvent obtaining an organic phase comprising at least parts of the amine of general formula (IIa); and an aqueous phase comprising at least parts of the anion of general formula (IIIa)

(IIIa), wherein n is zero or 1; and wherein the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; wherein the anion of general formula (IIIa) is preferably selected from the group consisting of diphenylacetate, 2,2-diphenylpropionate, 3,3-diphenylpropionate, 3,4-dichloro-benzoate, 3,4-dinitro-benzoate and 4-chloro-3-nitro-benzoate, more preferably from the group consisting of diphenylacetate, 2,2-diphenylpropionate, 3,3-diphenylpropionate, more preferably 2,2-diphenylpropionate or 3,3-diphenylpropionate, more preferably 3,3-diphenylpropionate.

The water immiscible organic solvent according to (vi) has preferably a $K_{OW}$ value of at least 0.5, more preferably of at least 0.6, more preferably of at least 0.7, more preferably of at least 0.8. According to a preferred embodiment, the water immiscible organic solvent according to (vi) is selected from the group of ethers, more preferably from the group of aliphatic ethers, more preferably MTBE (methyl-tert-butylether).

According to a further preferred embodiment, the method further comprises, preferably in addition to (i), (ii), (iii), (iv), (v) and (vi):

(vii-a) removal of the water immiscible organic solvent from the organic phase obtained in (vi) thereby obtaining the amine of general formula (IIa), (IIa), wherein $R^1$ and $R^2$ are as defined for general formula (I).

According to an alternative preferred embodiment, the method further comprises, preferably in addition to (i), (ii), (iii), (iv), (v) and (vi):

(vii-b) adding at least one acid HX to the organic phase obtained according to (vi), preferably HCl, thereby obtaining a salt of general formula (IV)

(IV), wherein $R^1$ and $R^2$ are as defined for general formula (I) and (II) and X is an ion based on the at least one acid HX, preferably Cl.

According to an alternative preferred embodiment, the method further comprises, preferably in addition to (i), (ii), (iii), (iv), (v), (vi) and (vii-a) or in addition to (i), (ii), (iii), (iv), (v), (vi) and (vii-b):

(viii) optionally precipitating the at least one carboxylic acid of general formula (III)

(III), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; preferably the at least one carboxylic acid being selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA), more preferably form the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA, from the aqueous phase obtained according to (vi) by adjusting the pH to a value in the range of from 0 to 6, preferably by addition of HCl, and (ix) optionally recycling the at least one carboxylic acid precipitated according to (viii) to the process, preferably to step (ii).

The present invention also relates to an amino salt compound obtained or obtainable by the method as described above.

In another aspect, the present invention relates to an amino salt compound comprising a cation of general formula (II)

(II), wherein $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero) aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aliphatic or aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; or $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol; and an anion of general formula (IIIa)

(IIIa), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring.

Preferably, the anion of general formula (IIIa) of the amine salt compound is selected from the group consisting of diphenylacetate, 2,2-diphenylpropionate, 3,3-diphenylpropionate, 3,4-dichloro-benzoate, 3,4-dinitro-benzoate and 4-chloro-3-nitro-benzoate, more preferably from the group consisting of diphenylacetate, 2,2-diphenylpropionate, 3,3-diphenylpropionate, more preferably 2,2-diphenylpropionate or 3,3-diphenylpropionate, more preferably 3,3-diphenylpropionate.

According to a preferred embodiment of the amino salt compound, $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5- alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aliphatic or aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

More preferably, the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy. According to a further preferred embodiment of the amino salt compound, the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy. According to a further preferred embodiment of the amino salt compound, the residue $R^1$ is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, C5-C20-cycloalkinyl, C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy. According to a further preferred embodiment of the amino salt compound, the residue $R^1$ is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, iso-propyl, cyclohexyl and phenyl, wherein phenyl has at least one substituent selected from the group consisting of hydrogen atom, halogen atom, preferably fluoro or chloro, and methoxy, preferably meta- or para-methoxy.

For $R^1$ being branched or unbranched C2-C20-alkyl or branched or unbranched C2-C20-alkenyl, a preferred embodiment relates to $R^1$ being branched or unbranched C4-C20-alkyl or branched or unbranched C4-C20-alkenyl.

According to a preferred embodiment of the amino salt compound, the residue $R^2$ is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy. Preferably, the residue $R^2$ is selected from the group consisting of branched or unbranched C1-C3-alkyl, $R^2$ being preferably methyl.

In a preferred embodiment, the combination of $R^1$, $R^{1a}$ being a perfluorinated alkyl is excluded. The same applies for $R^2$ and $R^{2a}$, i.e. the combination of $R^2$ and $R^{2a}$ being a perfluorinated alkyl is excluded as well. In other words, neither the combination of $R^1$ and $R^{1a}$ nor the combination of $R^2$ and $R^{2a}$ is a perfluorinated alkyl.

Regarding the embodiment wherein $R^1$ and $R^2$ together form a C3-C10-cycloalkyl or a C3-C10-cycloalkenyl, the number of C atoms indicated includes the carbonyl C atom situated between $R^1$ and $R^2$.

The present invention in another aspect relates to a composition comprising a) an amine of general formula (IIa)

(IIa), wherein $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero) aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy;

or $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol;

and b) at least one carboxylic acid of general formula (III) (III), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group; and the residue $R^5$ is hydrogen atom or methyl or absent if $R^3$ and $R^4$ together form a phenyl ring, wherein the at least one carboxylic acid is present in its protonated form or as carboxylate with a suitable counter ion.

According to a preferred embodiment of the composition, $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

More preferably, the at least one carboxylic acid according to (b) is a carboxylic acid selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA), more preferably form the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA.

According to a further preferred embodiment of the composition, the residue $R^1$ of the amine according to (a) is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy. Preferably, the residue $R^1$ of the amine according to (a) is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy. More preferably, the residue $R^1$ of the amine according to (a) is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, and C5-C20-cycloalkinyl, C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy. More preferably, the residue $R^1$ of the amine according to (a) is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, iso-propyl, cyclohexyl and phenyl, wherein phenyl has at least one substituent selected from the group consisting of hydrogen atom, halogen atom, preferably fluoro or chloro, and methoxy, preferably meta- or para-methoxy.

For $R^1$ being branched or unbranched C2-C20-alkyl or branched or unbranched C2-C20-alkenyl, a preferred embodiment relates to R1 being branched or unbranched C4-C20-alkyl or branched or unbranched C4-C20-alkenyl.

According to a further preferred embodiment of the composition, the residue $R^2$ of the amine according to (a) is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy. Preferably, the residue $R^2$ of the amine according to (a) is selected from the group consisting of branched or unbranched C1-C3-alkyl, $R^2$ being preferably methyl.

In a preferred embodiment of the composition, the combination of $R^1$, $R^{1a}$ being a perfluorinated alkyl is excluded. The same applies for $R^2$ and $R^{2a}$, i.e. the combination of $R^2$ and $R^{2a}$ being a perfluorinated alkyl is excluded as well. In other words, neither the combination of $R^1$ and $R^{1a}$ nor the combination of $R^2$ and $R^{2a}$ is a perfluorinated alkyl.

Regarding the embodiment of the composition, wherein $R^1$ and $R^2$ together form a C3-C10-cycloalkyl or a C3-C10-cycloalkenyl, the number of C atoms indicated includes the carbonyl C atom situated between $R^1$ and $R^2$.

According to a preferred embodiment of the composition, the composition comprises the amine according to (a) in an amount in the range of from 90 to 99.9 weight-%, preferably in an amount in the range of from 95 to 99.9 weight-%, more preferably in an amount in the range of from 98 to 99.9 weight-%. According to a further preferred embodiment of the composition, the composition comprises the at least one carboxylic acid according to (b) (protonated form or carboxylate with a suitable counter ion) in an amount of at least 0.003 weight-%, preferably in an amount in the range of from 0.003 to 5 weight-%, more preferably in an amount in the range of from 0.003 to 3 weight-%.

Below, the investigations carried out by the inventors are described in more detail:

As described above, commercially readily available aliphatic, aromatic and heteroaromatic carboxylic acids (R—COOH) were selected and screened as their respective carboxylate salts towards common amines from a transaminase-catalyzed reaction. 1-phenylethylamine and substituted derivatives 2a-f thereof served as model product amines and were compared with typical donor amines such as isopropylamine 3, racemic 2-butylamine, DL-alanine and L-alanine. The straight-forward screening approach especially resulted in the identification of two benzylbenzene-based acids and three benzoic acid derivatives that matched the required criteria: DPAA, 3DPPA, 34CA, 34NA and 43CNA. In addition, 2DPPA was identified as suitable carboxylic acid.

For example, the isopropylamine salt of 4-chloro-3-nitrobenzoic acid (43CNA) 5 shows a very high solubility of 993 $mmol \cdot l^1$, while the 1-phenylethylamine salt of 43CNA 6a is considerable less soluble with 22 $mmol \cdot l^{-1}$. As stated by Le Chatelier's principle, the solubility of amine salts can be further reduced if an over-stoichiometric amount of carboxylate is added to the mother liquor, which pushes the equilibrium from the dissociated forms (present in solution) towards its non-dissociated solid salt form.

Aside the general solubility difference, the applicability of these 3 acids—43CNA, DPAA and 3DPPA—was tested with 7 exemplary amine transaminases from *Aspergillus* fumigates (AfATA), *Gibberella zeae* (GzATA), *Neosartorya fischeri* (NfATA), *Aspergillus oryzae* (AoATA), *Aspergillus terreus* (AtATA), *Mycobacterium vanbaalenii* (MvATA) and *Silicibacter pomeroyi* (SpATA) (FIG. 1). The results show that almost all investigated amine transaminases are already strongly inhibited by 50 mM of the more soluble acids 43CNA and DPAA. Herein MvATA and SpATA were identified as the most stable enzymes. A noticeable exception from these results is acid 3DPPA, which is only sparingly soluble in buffered solutions. This effectively limits the carboxylate concentration in aqueous solution to a maximum of ≤25 mM, depending on temperature and pH, while the excess of solid 3DPPA remains in the reaction mixture. This low 3DPPA-concentration also does not significantly inhibit the investigated ATAs. Fortunately, the investigated 3DPPA-salts exhibit the lowest solubility of product amine salt 6, which fits perfectly into the above mentioned ISPC-requirements (see Example section, Tables 4 and 5). Consequently, 3DPPA was identified as the most valuable acid for the application in a crystallization-based in situ-product removal (ISPR) of amine 2 from an amine transaminase-catalyzed reaction.

Figure 2:
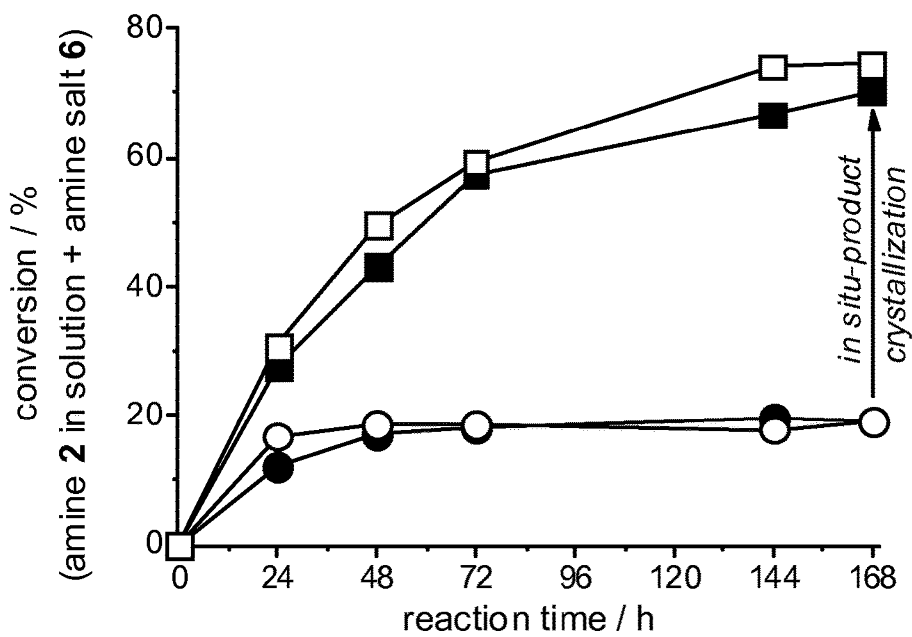
FIG. 2 Time progression curves for the SpTA-catalyzed formation of (S)-1-phenylethyl-amine with and without in situ-product crystallization (ISPC); □-whole cells or ■-cell extract with 125 mM 3DPPA, O-whole cells or •-cell extract without 3DPPA; Conditions: 200 mM phosphate buffer pH 7.5, 100 mM acetophenone, 250 mM isopropylamine, 15 mg·mL$^{-1}$ lyophilized cell extract or whole cells, 30° C.

The use of 3DPPA in combination with an exemplary SpATA-catalyzed conversion of 100 mM acetophenone 1a to (S)-1-phenylethylamine shows clearly the synthetic advantage of an acid-based ISPC (FIG. 2). The classical reaction approach with a low donor amine concentration of only 250 mM isopropylamine yields a non-sufficient conversion of 19%. A simple addition of 1.25 eq. solid 3DPPA improved the overall conversion directly to ca. 75%, regardless of the use as a whole cell biocatalyst or partially purified cell extract. The majority of product 2 is afterwards present as solid salt 6, which can be almost quantitatively recovered by filtration after cooling the reaction mixture to 0° C. Consequently, this ISPC-concept with 3DPPA translates to a more atom-efficient synthesis since less donor amine is required and a simplified downstream processing-approach is facilitated (see below). Noteworthy, the low solubility of 3DPPA does not limit the crystallization of product amine salt since the constant removal of 3DPPA from aqueous solution is continuously compensated back to its original solubility limit by a simultaneous dissolution of 3DPPA (from excess solid 3DPPA).

The shown ISPC-concept with acid 3DPPA was also successfully used for the SpATA-catalyzed conversion of selected acetophenone derivatives 1b-g and further non-aromatic substrates 1h-k (Table 2).

TABLE 2

ISPC-supported SpATA-catalyzed synthesis of chiral amines

| substrate | $R^{(0)}$ | x | conversion reference/% | conversion ISPC/% | e.e./%[a] |
|---|---|---|---|---|---|
| 1a | Ph | 0 | 19 | 75 | >99.5 |
| 1b | m-F—Ph | 0 | 21 | 69 | >99.5 |
| 1c | p-F—Ph | 0 | 11 | 61 | >99.5 |
| 1d | m-Cl—Ph | 0 | 8 | 46 | >99.5 |
| 1e | p-Cl—Ph | 0 | 8 | 65 | >99.5 |
| 1f | m-MeO—Ph | 0 | 10 | 37 | >99.5 |
| 1g | p-MeO—Ph | 0 | 4 | 8 | >99.5 |
| 1h | Cy | 0 | 0 | 8 | n.d. |
| 1i | Me | 3 | 37 | 72 | >99.5 |
| 1j | Me | 4 | 20 | 78 | 98.7 |
| 1k | iPr | 1 | 36 | 96 | n.d. |

[a]Values are given for the ISPC-supported reaction; Conditions: 200 mmM phosphate buffer pH 7.5, 100 mM substrate, 250 mM isopropylamine, 15 $mg \cdot mL^{-1}$ lyophilized whole cells, 30° C.; 125 mM 3DPPA for ISPC As expected, for all substrates low conversions were obtained without ISPC due to the low, but still over-stochiometric, use of 250 mM isopropylamine. A simple addition of 3DPPA increases product formation significantly for almost all investigated substrates. Improvements range between 2 and 8.1-fold with yields of up to 96% for 1 k, while the products are selectively crystallized as its 3DPPA-salts. The remaining mother liquor, including excess isopropylamine, can be directly reused for a further increase of atom efficiency of the transaminase-catalyzed reaction. Even higher donor amine concentrations will yield a further increase in conversion, but include the risk of an undesired crystallization of donor amine salt, which then eventually yields a decrease in product formation.

The isolation of product amine 2 is easily realized by dissolving product salt 6 in an aqueous solution at high pH, followed by an extraction and evaporation of the solvent, e.g. MTBE. Alternatively, the respective hydrochloride salt can be directly crystallized from the ether phase by a careful addition of concentrated HCl. In addition, the spent acid 3DPPA can also be precipitated from the remaining aqueous phase by acidification with concentrated HCl, due to its low solubility at low pH.

Summarizing, the presented in situ-product crystallization of an amine from a transaminase-catalyzed reaction by the addition of a selected acid/carboxylate presents a powerful synthetic alternative to the use of tailor-made donor amines and complex cascade reaction systems. The main advantages of this ISPC are a more atom-efficient use of classical, cheap donor amines and a simplified downstream processing-approach by simple filtration. The targeted product amine can be afterwards extracted from its salt and the applied 3DPPA acid easily recycled.

The present invention is further illustrated by the following embodiments and combinations of embodiments as indicated by the respective dependencies and back-references. In particular, it is noted that in each instance where a range of embodiments is mentioned, for example in the context of a term such as “The process of any one of embodiments 1 to 4”, every embodiment in this range is meant to be explicitly disclosed for the skilled person, i.e. the wording of this term is to be understood by the skilled person as being synonymous to “The process of any one of embodiments 1, 2, 3, and 4”.

1. Method for preparing an amino salt compound comprising:
   i) providing a carbonyl compound of general formula (I)
   (I),
   wherein
   $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and
   $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy;
   or
   $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol;
   ii) reacting the carbonyl compound provided according to (i) in the presence of a transaminase with
   ii-a) at least one primary amine; and
   ii-b) at least one carboxylic acid;
   thereby obtaining a mixture comprising an at least partially crystallized amino salt compound comprising
   a cation of general formula (II)
   (II),
   wherein $R^1$ and $R^2$ are as defined for general formula (I) and
   a carboxylate anion based on the at least one carboxylic acid added according to (ii-b).
2. The method according to embodiment 1, wherein the amino salt compound obtained according to (ii) has a solubility in water at pH 7 which is smaller than the solubility in water of the at least one primary amine added according to (ii-a).
3. The method according to embodiment 1 or 2, wherein the amino salt compound obtained according to (ii) has a solubility in water at pH 7≤30 mmol/l, preferably ≤25 mmol/l, more preferably ≤10 mmol/l.
4. The method according to any one of embodiments 1 to 3, wherein the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy;
5. The method according to any one of embodiments 1 to 4, wherein the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, wherein the hetero atom(s) is/are selected from oxygen, sulfur and nitrogen wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

6. The method according to any one of embodiments 1 to 5, wherein the residue $R^1$ is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, C5-C20-cycloalkinyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy.
7. The method according to any one of embodiments 1 to 6, wherein the residue $R^1$ is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, isopropyl, cyclohexyl and phenyl, wherein phenyl has at least one substituent $R^{1a}$ selected from the group consisting of hydrogen atom, halogen atom, preferably fluoro or chloro, and methoxy, preferably meta- or para-methoxy.
8. The method according to any one of embodiments 1 to 7, wherein the residue $R^2$ is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy.
9. The method according to any one of embodiments 1 to 8, wherein the residue $R^2$ is selected from the group of branched or unbranched C1-C3-alkyl, $R^2$ being preferably methyl.
10. The method according to any one of embodiments 1 to 9, wherein the transaminase according to (ii) is selected from the group of transaminases, preferably from the group of amine transaminases, more preferably selected from the group consisting of amine transaminase from *Aspergillus* fumigates (AfATA) according to SEQ ID NO 1, amine transaminase from *Gibberella zeae* (GzATA) according to SEQ ID NO 2, amine transaminase from *Neosartorya fischeri* (NfATA) according to SEQ ID NO 3, amine transaminase from *Aspergillus oryzae* (AoATA) according to SEQ ID NO 4, amine transaminase from *Aspergillus terreus* (AtATA) according to SEQ ID NO 5, amine transaminase from *Mycobacterium vanbaalenii* (MvATA) according to SEQ ID NO 6, amine transaminase from *Silicibacter pomeroyi* (SpATA) according to SEQ ID NO 7 and a homologue enzyme having sequence identity of at least 65% with any one of SEQ ID NO 1 to 7 and having the same function as the amine transaminase of SEQ ID NO 1 to 7, more preferably selected from the group consisting of the amine transaminase from *Mycobacterium vanbaalenii* (MvATA) according to SEQ ID NO 6, the amine transaminase from *Silicibacter pomeroyi* (SpATA) according to SEQ ID NO 7 and a homologue enzyme having sequence identity of at least 65% with any one of SEQ ID NO 6 or 7 and having the same function as the amine transaminase of SEQ ID NO 6 or 7.
11. The method according to embodiment 10, wherein the homologue enzyme has a sequence identity of at least 75%, preferably at least 85%, more preferably at least 90%, more preferably at least 95%, more preferably at least 98%, more preferably at least 99%, with any one of SEQ ID NO 1 to 7 and has the same function as the amine transaminase of SEQ ID NO 1 to 7.
12. The method according to any one of embodiments 1 to 11, wherein the at least one primary amine according to (ii-a) is used in non-protonated form or in protonated form with a suitable counter anion.
13. The method according to any one of embodiments 1 to 12, wherein the at least one primary amine according to (ii-a) is selected from the group of mono- and diamines having one to 10 carbon atoms, preferably from the group consisting of 1,5-diamino-pentane (cadaverine), alanine, 2-amino-butane (sec-butylamine) and 2-amino-propane, and is preferably 2-amino-propane (iso-propylamine) in its non-protonated or protonated form, wherein the protonated form is present in combination with a suitable anion.
14. The method according to any one of embodiments 1 to 13, wherein the at least one carboxylic acid according to (ii-b) is used in its protonated form or in deprotonated form with a suitable counter cation.
13. The method according to any one of embodiments 1 to 12, wherein the at least one carboxylic acid according to (ii-b) is a carboxylic acid of general formula (III) (III), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group; and the residue $R^5$ is hydrogen atom or methyl or absent if $R^3$ and $R^4$ together form a phenyl ring; preferably the at least one carboxylic acid according to (ii-b) is a carboxylic acid selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA), more preferably from the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA.

16. The method according to any one of embodiments 1 to 15, wherein the at least one primary amine according to (ii-a) and the at least one carboxylic acid according to (ii-b) are used as one or more salt(s) comprising the protonated form of the at least one primary amine and the deprotonated form of the at least one carboxylic acid, preferably as one salt comprising the protonated form of the at least one primary amine and the deprotonated form of the at least one carboxylic acid, more preferably as isopropyl ammonium 3,3-diphenylpropionate.

17. The method according to any one of embodiments 1 to 16, wherein the amino salt compound obtained according to (ii) comprises a cation of general formula (II)
(II),
wherein $R^1$ and $R^2$ are as defined for general formula (I), and an anion based on the at least one carboxylic acid, which is preferably an anion of general formula (IIIa)
(IIIa),
wherein n is zero or 1;
the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; wherein the anion of general formula (IIIa) is preferably selected from the group consisting of diphenylacetate, 2,2-diphenylpropionat, 3,3-diphenylpropioniat, 3,4-dichloro-benzoat, 3,4-dinitro-benzoat and 4-chloro-3-nitro-benzoat, more preferably form the group consisting of diphenylacetate, 2,2-diphenylpropionat, 3,3-diphenylpropioniat, more preferably 2,2-diphenylpropionat or 3,3-diphenylpropioniat, more preferably 3,3-diphenylpropioniat.
18. The method according any one of embodiments 1 to 17, wherein the reaction according to (ii) is carried out in an aqueous solution, which preferably comprises at least 80 weight-%, more preferably at least 90 weight-%, more preferably at least 95 weight-%, more preferably at least 98 weight-%, water, based on the overall weight of the aqueous solution.
19. The method according to embodiment 18, wherein the aqueous solution comprises a buffer, preferably selected from the group of tris(hydroxymethyl)aminomethane buffer (TRIS buffer), 3-(N-morpholino)propanesulfonic acid buffer (MOPS buffer), N,N-Bis(2-hydroxyethyl)-2-aminoethanesulfonic acid buffer (BES buffer), N-(tris(hydroxymethyl)methyl)glycine buffer (Tricine buffer), Carbonate buffer, N-cyclohexyl-2-aminoethanesulfonic acid buffer (CHES buffer), 4-(2-hydroxyethyl)-1-piperazineethanesulfonic acid buffer (HEPES buffer) and phosphate buffer, more preferably at least a phosphate buffer.
20. The method according to any one of embodiments 1 to 19, wherein the reaction according to (ii) is carried out at a pH value in the range of 6.0 to 9.5, preferably in the range of from 6.5 to 9.0, more preferably in the range of from 7.0 to 8.0.
21. The method according to any one of embodiments 1 to 20, wherein the reaction according to (ii) is carried out for a time period of at least one hour, preferably for a time in the range of from 1 to 1,000 hours, more preferably in the range of from 5 to 500 hours, more preferably in the range of from 10 to 200 hours.
22. The method according to any one of embodiments 1 to 21, wherein the reaction according to (ii) is carried out at a temperature in the range of from 10 to 50° C., preferably in the range of from 15 to 45° C., more preferably in the range of from 20 to 40° C., more preferably in the range of from 25 to 35° C.
23. The method according to any one of embodiments 1 to 22, wherein for the at least one carboxylic acid being a carboxylic acid according to general formula (III), wherein the residues $R^3$ and $R^4$ together form a phenyl ring, preferably a carboxylic acid selected from the group consisting of 3,4-dichloro-benzoic acid (34CA), 3,4-dinitro-benzoic acid (34NA) and 4-chloro-3-nitro-benzoic acid (43CNA), the concentration of the at least one carboxylic acid is kept in the range of from 0.001 to 50 mM, preferably in the range of form 1 to 45 mM, more preferably in the range of from 5 to 40 mM during step (ii).
24. The method according to any one of embodiments 1 to 22, wherein for the at least one carboxylic acid being a carboxylic acid according to general formula (III), wherein the residues $R^3$ and $R^4$ are each a phenyl ring, preferably a carboxylic acid selected from the group consisting of diphenylacetic acid (DPAA), 2,2-diphenylpropionic acid (2DPPA) and 3,3-diphenylpropionic acid (3DPPA), the concentration of the at least one carboxylic acid is 50 mM during step (ii).
25. The method according to any one of embodiments 1 to 24, further comprising:
iii) separating the at least partially crystallized amine salt compound obtained according to (ii) from the mixture thereby obtaining the crystallized amine salt compound.
26. The method according to embodiment 26, wherein separating the crystallized amine salt compound according to (iii) from the mixture is done by sedimentation, centrifugation or filtration, preferably by filtration.
27. The method according to any one of embodiments 1 to 24, further comprising:
(iv) optionally washing the separated crystallized amino salt compound obtained according to (iii), preferably with water or an organic solvent or a mixture thereof, more preferably with water or methyl tert-butyl ether or a mixture thereof, thereby obtaining a washed crystallized amino salt compound;
(v) dissolving the crystallized amino salt compound obtained according to (iii) or optionally the washed crystallized amino salt compound obtained according to (iv) in an aqueous solution having a pH value in the range of from 10 to 14 comprising at least one base, preferably a base comprising a hydroxide ion, thereby obtaining an aqueous solution comprising an amine of general formula (IIa)
(IIa),
wherein $R^1$ and $R^2$ are as defined for general formula (I);
(vi) extracting the aqueous solution obtained according to (v) at least once with a water immiscible organic solvent obtaining an organic phase comprising at least parts of the amine of general formula (IIa);
and an aqueous phase comprising at least parts of the anion of general formula (IIIa)
(IIIa),
wherein n is zero or 1; and wherein the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; wherein the anion of general formula (IIIa) is preferably selected from the group consisting of diphenylacetate, 2,2-diphenylpropionat, 3,3-diphenylpropioniat, 3,4-dichloro-benzoat, 3,4-dinitro-benzoat and 4-chloro-3-nitro-benzoat, more preferably from the group consisting of diphenylacetate, 2,2-diphenylpropionat, 3,3-diphenylpropioniat, more preferably 2,2-diphenylpropionat or 3,3-diphenylpropioniat, more preferably 3,3-diphenylpropioniat.

28. The method according to embodiment 27, further comprising:

(vii-a) removal of the water immiscible organic solvent from the organic phase obtained in (vi) thereby obtaining the amine of general formula (IIa), (IIa), wherein $R^1$ and $R^2$ are as defined for general formula (I).

29. The method according to embodiment 27 further comprising:

(vii-b) adding at least one acid HX to the organic phase obtained according to (vi), preferably HCl, thereby obtaining a salt of general formula (IV)

(IV), wherein $R^1$ and $R^2$ are as defined for general formula (I) and (II) and X is an ion based on the at least one acid HX, preferably Cl.

30. The method according to embodiment 27 or 28, wherein the water immiscible organic solvent according to (vi) has a $K_{OW}$ value of at least 0.5, more preferably of at least 0.6, more preferably of at least 0.7, more preferably of at least 0.8.

31. The method according to any one of embodiments 27 to 30, further comprising:

(viii) optionally precipitating the at least one carboxylic acid of general formula (III)

(III), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring; preferably the at least one carboxylic acid being selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA), more preferably form the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA, from the aqueous phase obtained according to (vi) by adjusting the pH to a value in the range of from 0 to 6, preferably by addition of HCl, and (ix) optionally recycling the at least one carboxylic acid precipitated according to (viii) to the process, preferably to step (ii).

32. An amino salt compound obtained or obtainable by the method according to any one of embodiments 1 to 31.

33. An amino salt compound comprising a cation of general formula (II)

(II), wherein $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero) aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aliphatic or aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; or $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol;

and an anion of general formula (IIIa)

(IIIa), wherein n is zero or 1;

the residues $R^3$ and $R^4$ are both phenyl or together form a phenyl ring, wherein each phenyl ring has at least one further substituent selected from the group consisting of hydrogen atom, halogen atom, preferably chloro, and nitro group and the residue $R^5$ is hydrogen atom or methyl or absent if $R^3$ and $R^4$ together form a phenyl ring.

34. The amino salt compound according to embodiment 33, wherein the anion of general formula (IIIa) is preferably selected from the group consisting of diphenylacetate, 2,2-diphenylpropionate, 3,3-diphenylpropionate, 3,4-dichloro-benzoate, 3,4-dinitro-benzoate and 4-chloro-3-nitro-benzoate, more preferably from the group consisting of diphenylacetate, 2,2-diphenylpropionate, 3,3-diphenylpropionate, more preferably 2,2-diphenylpropionate or 3,3-diphenylpropionate, more preferably 3,3-diphenylpropionate.

35. The amino salt compound according to embodiment 33 or 34, wherein the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy;

36. The amino salt compound according to any one of embodiments 33 to 35, wherein the residue $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

37. The amino salt compound according to any one of embodiments 33 to 36, wherein the residue $R^1$ is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, C5-C20-cycloalkinyl, C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy.

38. The amino salt compound according to any one of embodiments 33 to 37, wherein the residue $R^1$ is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, iso-propyl, cyclohexyl and phenyl, wherein phenyl has at least one substituent selected from the group consisting of hydrogen atom, halogen atom, preferably fluoro or chloro, and methoxy, preferably meta- or para-methoxy.

39. The amino salt compound according to any one of embodiments 33 to 38, wherein the residue $R^2$ is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy.

40. The amino salt compound according to any one of embodiments 33 to 39, wherein the residue $R^2$ is selected from the group consisting of branched or unbranched C1-C3-alkyl, $R^2$ being preferably methyl.

41. A composition comprising
  a) an amine of general formula (IIa)
    (IIa),
    wherein
    $R^1$ is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein in case of more than one (hetero)aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; and
    $R^2$ is selected from the group consisting of hydrogen atom, branched or unbranched C1-C5-alkyl, branched or unbranched C1-C5-alkyl-O—C1-C5-alkyl, branched or unbranched C1-C10-alkoxy, C5-C10-aryl, C6-C10-alkylaryl and C6-C10-arylalkyl, wherein in case of more than one aromatic ring system the ring systems are condensed or separate, wherein each residue $R^2$ has at least one substituent $R^{2a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy; or
    $R^1$, $R^2$ together form a C3-C10-cycloalkyl or C3-C10-cycloalkenyl, wherein the C3-C10-cycloalkyl or C3-C10-cycloalkenyl each has at least one substituent $R^x$ selected from the group consisting of hydrogen atom, C1-C5-alkyl, C1-C4-heteroalkyl and C1-C5-alkyl-$R^y$, wherein $R^y$ is hydroxyl or thiol;
    and
  b) at least one carboxylic acid of general formula (III)
    (III),
    wherein n is zero or 1;
    the residues $R^3$ and $R^4$ are both phenyl or together form a phenyl ring, wherein each phenyl ring has at least one further substituent selected from the group consisting of hydrogen atom, halogen atom, preferably chloro, and nitro group; and the residue $R^5$ is hydrogen atom or methyl or absent if $R^3$ and $R^4$ together form a phenyl ring, wherein the at least one carboxylic acid is present in its protonated form or as carboxylate with a suitable counter ion.

42. The composition according to embodiment 41, wherein the at least one carboxylic acid according to (b) is a carboxylic acid selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA), more preferably form the group consisting of diphenylacetic acid (DPAA), 2,2-diphenylpropionic acid (2DPPA) and 3,3-diphenylpropionic acid (3DPPA), more preferably 2,2-diphenylpropionic acid (2DPPA) or 3,3-diphenylpropionic acid (3DPPA), more preferably at least 3DPPA.

43. The composition according to embodiment 41 or 42, wherein the residue $R^1$ of the amine according to (a) is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, C4-C20-heteroaryl, C5-C20-alkylheteroaryl and C5-C20-heteroarylalkyl, wherein the hetero atom(s) in C4-C20-heteroaryl, C5-C20-alkylheteroaryl and C5-C20-heteroarylalkyl is/are oxygen or sulfur and the hetero atom(s) in C2-C20-heteroalkyl and C3-C20-cyclic heteroalkyl, is/are selected from oxygen, sulfur and nitrogen, wherein in case of more than one (hetero) aliphatic or (hetero)aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

44. The composition according to any one of embodiments 41 to 43, wherein the residue $R^1$ of the amine according to (a) is selected from the group consisting of branched or unbranched C2-C20-alkyl, branched or unbranched C2-C20-alkenyl, branched or unbranched C2-C20-alkinyl, branched or unbranched C1-C5-alkyl-O—C1-C5-alkyl, branched or unbranched C1-C10-alkoxy, C4-C20-cycloalkyl, C5-C20-cycloalkenyl, C5-C20-cycloalkinyl, C5-C20-aryl, C6-C20-alkylaryl, C6-C20-arylalkyl, C2-C20-heteroalkyl, C3-C20-cyclic heteroalkyl, wherein in case of more than one aliphatic or aromatic ring system the ring systems are condensed or separate, wherein each residue $R^1$ has at least one substituent $R^{1a}$ selected from the group consisting of hydrogen atom, halogen atom (F, Cl, Br, I), hydroxyl, thiol, C1-C3 thioester, C1-C3-thioether, C1-C3-alkyl and C1-C3-alkoxy.

45. The composition according to any one of embodiments 41 to 44, wherein the residue $R^1$ of the amine according to (a) is selected from the group consisting of branched or unbranched C2-C20-alkyl, branched or unbranched C2-C20-alkenyl, branched or unbranched C2-C20-alkinyl, C4-C20-cycloalkyl, C5-C20-cycloalkenyl, and C5-C20-cycloalkinyl, C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy.

46. The composition according to any one of embodiments 41 to 45, wherein the residue $R^1$ of the amine according to (a) is selected from the group consisting of branched or unbranched C2-C10-alkyl, C5-C10-cycloalkyl and C5-C20-aryl, wherein in case of more than one aliphatic or aromatic ring system the ring systems are condensed or separate, wherein each residue $R^1$ has at least one substituent $R^{1a}$ selected from the group consisting of hydrogen atom, halogen atom, C1-C3-alkyl and C1-C3-alkoxy; $R^1$ being preferably selected from the group consisting of methyl, iso-propyl, cyclohexyl and phenyl, wherein phenyl has at least one substituent selected from the group consisting of hydrogen atom, halogen atom, preferably fluoro or chloro, and methoxy, preferably meta- or para-methoxy.

47. The composition according to any one of embodiments 41 to 46, wherein the residue $R^2$ of the amine according to (a) is selected from the group consisting of hydrogen atom, branched or unbranched C1-C5-alkyl, wherein each residue $R^2$ has at least one substituent $R^{2a}$ selected from the group consisting of hydrogen atom, halogen atom, C1-C3-alkyl and C1-C3-alkoxy.

48. The composition according to any one of embodiments 41 to 47, wherein the residue $R^2$ of the amine according to (a) is selected from the group consisting of branched or unbranched C1-C3-alkyl, $R^2$ being preferably methyl.

49. The composition according to any one of embodiments 41 to 48, wherein the composition comprises the amine according to (a) in an amount in the range of from 90 to 99.9 weight-%, preferably in an amount in the range of from 95 to 99.9 weight-%, more preferably in an amount in the range of from 98 to 99.9 weight-%.

50. The composition according to any one of embodiments 41 to 49, wherein the composition comprises the at least one carboxylic acid according to (b) (protonated form or carboxylate with a suitable counter ion) in an amount of at least 0,003 weight-%, preferably in an amount in the range of from 0,003 to 5 weight-%, more preferably in an amount in the range of from 0.003 to 3 weight-%.

EXPERIMENTAL SECTION

1. General Information

Materials: All chemicals were obtained from commercial suppliers and used as received. Deionized water was used throughout this study. The investigated enzymes (raw extract and whole cells) were received from Enzymicals AG (Greifswald, Germany) as lyophilizates; ECS-ATA01 (TA from *Aspergillus* fumigates, SEQ ID NO. 1), ECS-ATA02 (TA from *Gibberella zeae*, SEQ ID NO.2), ECS-ATA03 (TA from *Neosartorya fischeri*, SEQ ID NO.3), ECS-ATA04 (TA from *Aspergillus oryzae*, SEQ ID NO. 4), ECS-ATA05 (TA from *Aspergillus terreus*, SEQ ID NO. 5), ECS-ATA07 (TA from *Mycobacterium vanbaalenii*, SEQ ID NO. 6) and ECS-ATA08 (TA from *Silicibacter pomeroyi*, SEQ ID NO. 7).

Gas chromatography: Conversion was measured with a Trace 1310 gaschromatograph by Thermo Scientific (Dreieich, Germany), equipped with a 1300 flame ionization detector and a Chirasil-Dex-CB-column (25 m×0.25 mm×0.25 μm). n-Decane was used as internal standard in all measurements. Temperatures of injector and detector were set to 250° C.

Temperature Programs:

Compounds 1a/2a, 1b/2b and 1c/2c: start at 90° C., followed by a heating rate of 2 K/min to 114° C. and 20 K/min to 150° C.

Compounds 1d/2d, 1e/2e, 1f/2f and 1g/2g: Start at 90° C., followed by a heating rate of 2 K/min to 100° C., 20 K/min to 130° C., 2 K/min to 150° C. and 20 K/min to 160° C.

Compounds 1i/2i, 1j/2j, 1k/2k: Start at 90° C., followed by a heating rate of 2 K/min to 96° C. and 20 K/min to 110° C.

HPLC: Enantiomeric excess was measured with a 1100 Series HPLC by Agilent (Santa Clara, California, United States), equipped with a diode array detector, with a Chiralcel OD-H (250 mm length, 4.6 mm internal diameter, particle size: 5 μm) and a flow of 1 mL/min at 25° C. Eluent composition for the respective amine: 99% n-heptane/1% ethanol for 2f; 98% n-heptane/2% ethanol for 2b, 2c and 2g; 95% n-heptane/5% ethanol for 2a, 2d and 2e Enzyme Activity Assay: Enzyme activity was measured at a wave length of 245 nM with the spectrophotometer Specord 200 from Analytik Jena (Jena, Germany). Extinction coefficient of acetophenone: 11.852 $(mM\cdot cm)^{-1}$.

Composition of the assay: 250 μL buffer solution, 250 μL 10 mM (S)-1-phenylethylamine in buffer solution, 250 μL 10 mM sodium pyruvate in buffer solution and 250 μL enzyme sample in buffer solution with 0.1 mM pyridoxal phosphate. All measurements were measured against a reference solution, whereas the enzyme solution was replaced with 200 μL buffer solution and 50 μL of 10 mM pyridoxal phosphate in buffer solution. Buffer solution: 50 mM phosphate buffer pH 8 with 0.25% DMSO.

2. Investigated Acids for the In Situ-Product Crystallization of Amines

A total of 79 acids were chosen for the screening procedure of relevant amines (table 3). The selection is mostly based on commercial availability and stability in aqueous solution.

TABLE 3

List of investigated acids for the ISPC-concept

| entry | abbreviation | full name | chemical structure | molar mass [g/mol] |
|---|---|---|---|---|
| 1 | FCC | Formic acid | | 46.03 |
| 2 | ACC | Acetic acid | | 60.05 |
| 3 | PPA | Propionic acid | | 74.08 |
| 4 | BCA | Butyric acid | | 88.11 |
| 5 | VCA | Valeric acid | | 102.13 |
| 6 | HXCA | Hexanoic acid | | 116.16 |
| 7 | HA | Heptanoic acid | | 130.19 |
| 8 | CCA | Caprylic acid | | 144.21 |
| 9 | nNA | Nonanoic acid | | 158.23 |
| 10 | DCC | Decanoic acid | | 172.27 |
| 11 | OA | Oxalic acid | | 90.03 |
| 12 | MA | Malonic acid | | 104.06 |
| 13 | SCCA | Succinic acid | | 118.09 |
| 14 | GA | Glutaric acid | | 132.12 |
| 15 | APS | Adipic acid | | 146.14 |
| 16 | PIA | Pimelic acid | | 160.17 |
| 17 | SBCA | Suberic acid | | 174.20 |
| 18 | AA | Azelaic acid | | 188.22 |
| 19 | SCA | Sebacic acid | | 202.25 |
| 20 | TMPA | Trimethyl-pyruvic acid | | 130.14 |
| 21 | GCA | Glycolic acid | | 76.05 |
| 22 | TG | Tiglic acid | | 100.116 |
| 23 | IS | Itaconic acid | | 130.10 |
| 24 | FA | Fumaric acid | | 116.07 |
| 25 | LMA | L-Malic acid | | 134.09 |
| 26 | DTA | D-(-)-Tartaric acid | | 150.09 |
| 27 | LTA | L-(-)-Tartaric acid | | 150.09 |
| 28 | DBDT | Dibenzoyl-D-tartaric acid | | 358.30 |
| 29 | CHCA | Cyclohexane carboxylic acid | | 128.17 |
| 30 | DQA | D-(-)-Quinic acid | | 192.17 |

TABLE 3-continued

List of investigated acids for the ISPC-concept

| entry | abbreviation | full name | chemical structure | molar mass [g/mol] |
|---|---|---|---|---|
| 31 | BZA | Benzoic acid | | 122.12 |
| 32 | SA | Salicylic acid | | 138.12 |
| 33 | ASA | Acetyl-salicylic acid | | 180.16 |
| 34 | 4HBA | 4-Hydroxy-benzoic acid | | 138.12 |
| 35 | 35HBA | 3,5-Dihydroxy-benzoic acid | | 154.12 |
| 36 | 25DHBA | 2,5-Dihydroxy-benzoic acid | | 154.12 |
| 37 | VA | Vanillic acid | | 168.15 |
| 38 | IVA | Isovanillic acid | | 168.15 |
| 39 | 43HNBA | 4-Hydroxy-3-nitrobenzoic acid | | 183.12 |
| 40 | 3NA | 3-Nitrobenzoic acid | | 167.12 |
| 41 | 24CNA | 2-Chloro-4-nitrobenzoic acid | | 201.56 |
| 42 | 25CNA | 2-Chloro-5-nitrobenzoic acid | | 201.56 |
| 43 | 32CNA | 3-Chloro-2-nitrobenzoic acid | | 201.56 |
| 44 | 42CNA | 4-Chloro-2-nitrobenzoic acid | | 201.56 |
| 45 | 43CNA | 4-Chloro-3-nitrobenzoic acid | | 201.56 |
| 46 | 34NA | 3,4-Dinitro-benzoic acid | | 212.12 |
| 47 | 435CNBA | 4-Chloro-3,5-dinitrobenzoic acid | | 246.56 |
| 48 | 35DNOT | 3,5-Dinitro-o-toluic acid | | 226.14 |
| 49 | 26FBA | 2,6-Difluoro-benzoic acid | | 158.10 |
| 50 | 2CA | 2-Chloro-benzoic acid | | 156.57 |
| 51 | 34CA | 3,4-Dichloro-benzoic acid | | 191.01 |
| 52 | RMA | (R)-Mandelic acid | | 152.15 |
| 53 | SMA | (S)-Mandelic acid | | 152.15 |
| 54 | CMA | R-(-)-2-Chloro-mandelic acid | | 186.59 |
| 55 | PAA | Phenylacetic acid | | 136.15 |
| 56 | PMA | Phenyl-malonic acid | | 180.16 |
| 57 | PA | Phthalic acid | | 166.13 |
| 58 | TPA | Terephthalic acid | | 166.13 |
| 59 | BTA | 1,2,4,5 Benzene-tetra-carboxylic acid | | 254.15 |
| 60 | CA | Caffeic acid | | 180.16 |
| 61 | FCA | Ferulic acid | | 194.18 |
| 62 | 34HHCAA | 3,4-Dihydroxy-hydro-cinnamic acid | | 182.17 |

TABLE 3-continued

List of investigated acids for the ISPC-concept

| entry | abbreviation | full name | chemical structure | molar mass [g/mol] |
|---|---|---|---|---|
| 63 | PCPA | 1-Phenylcyclo-pentane-carboxylic acid | | 190.24 |
| 64 | BPA | 4-Biphenyl-carboxylic acid | | 198.22 |
| 65 | DPAA | Diphenyl-acetic acid | | 212.24 |
| 66 | 2DPPA | 2,2'-Diphenyl-propionic acid | | 226.27 |
| 67 | BA | Benzilic acid | | 228.25 |
| 68 | 3DPPA | 3,3-Diphenyl-propionic acid | | 226.27 |
| 69 | TPAA | Triphenyl-acetic acid | | 288.34 |
| 70 | TPPA | 3,3,3-Triphenyl-propionic acid | | 302.37 |
| 71 | INA | Isonicotinic acid | | 123.11 |
| 72 | NCC | Nicotinic acid | | 123.11 |
| 73 | PCC | Picolinic acid | | 123.11 |
| 74 | 2HNA | 2-Hydroxy-nicotinic acid | | 139.11 |
| 75 | 2FCA | 2-Furoic acid | | 112.08 |
| 76 | 3FCA | 3-Furoic acid | | 112.08 |
| 77 | 25FDCA | 2,5-Furan-dicarboxylic acid | | 156.09 |
| 78 | PFA | 5-Phenyl-2-furoic acid | | 188.18 |
| 79 | 2TPCA | 2-Thiophene-carboxylic acid | | 128.15 |

3. Precipitation Screening for Suitable Acids

Screening of suitable acids was conducted with enantiomerically pure 1-phenylethylamine 2a and 6 derivatives thereof as model product amines at 50 mM. As typical donor amines racemic 2-butylamine, racemic alanine & L-alanine (at 100 mM) and isopropylamine 3 & racemic 1-phenylethylamine rac-2a (at 250 mM & 1000 mM) were chosen (scheme 3). The choice of the respective product amine enantiomer is not relevant for solubility screening since enantiomers have identical physical-chemical properties (incl. solubility), except its rotation of plane-polarized light in opposite directions. Results with racemic amines may differ significantly.

Scheme 3
Exemplary product and donor amines for acid screening donor amines

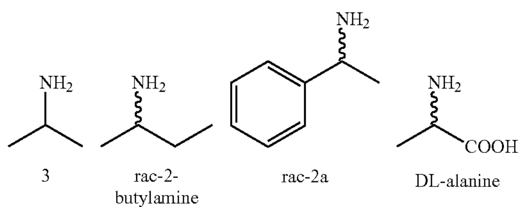

-continued

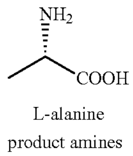

L-alanine product amines

2a

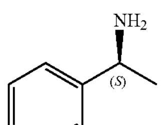

2b

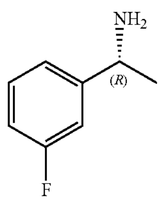

2c

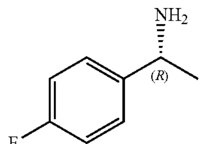

2d

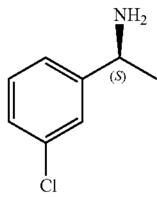

2e

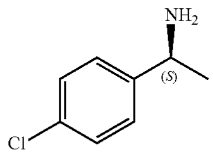

2f

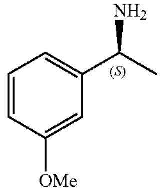

2g

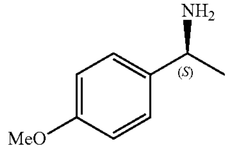

Neutralized Acid Solutions:

All 79 separate 400 mM acid solutions (typically 20 mL) were prepared by dissolving the respective acid in 50 mM phosphate buffer pH 7.5. Afterwards within all resulting solutions the pH was carefully adjusted back to 7.5. Please note that acids with low aqueous solubility may require multiple pH adjustments due to an additional dissolution process after its previous pH-adjustment. Acid solution with a remaining solid fraction were filtered and used in their resulting (unknown) concentration.

Neutralized Amine Solutions:

The selected exemplary product amines were dissolved in 50 mM phosphate buffer pH 7.5 with a concentration of 100 mM each and the pH carefully adjusted back to 7.5. Similarly solutions of the donor amines were prepared (200 mM for racemic 2 butylamine, racemic alanine and L-alanine and 500 mM & 2000 mM for isopropylamine and racemic 1-phenylethylamine).

Precipitation Screening Procedure

Figure 3:
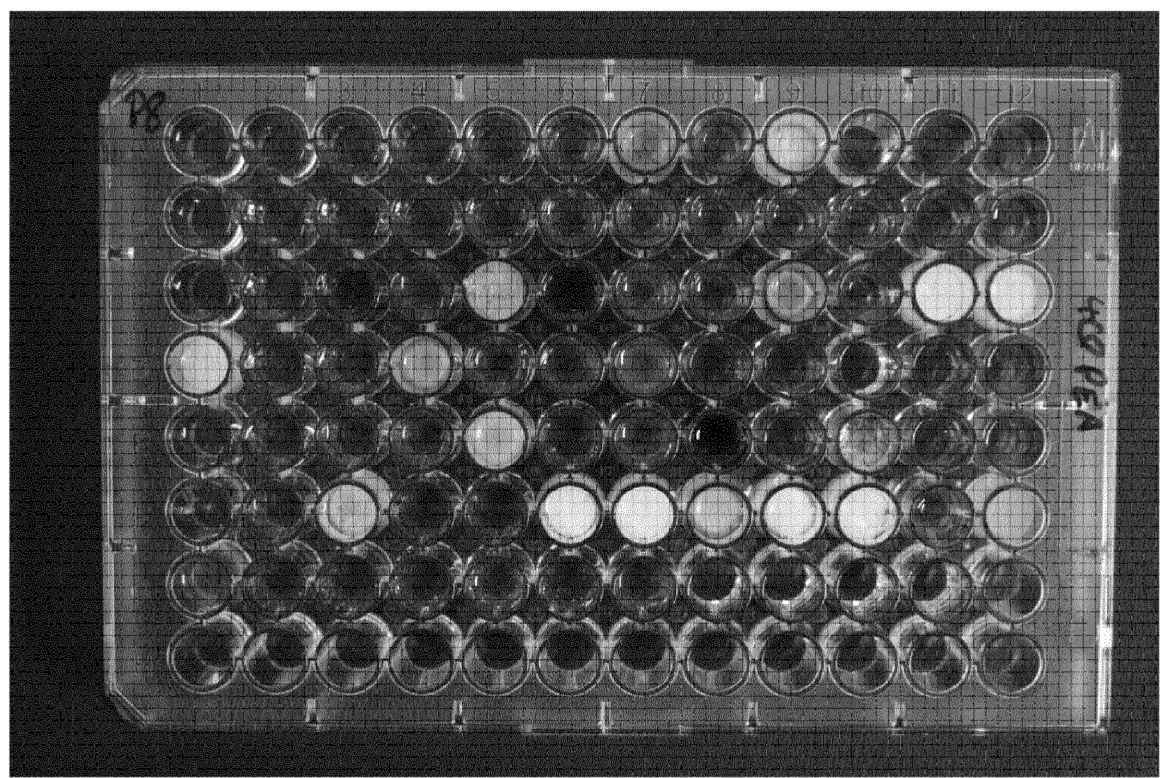
FIG. 3: Exemplary result for the precipitation of (S)-4-Chloro-1-phenylethylamine salts.

200 µl fractions of the neutralized acid solutions (79 in total) were given each into a 96 well plate and their position documented. Afterwards 200 µl of one neutralized amine solution was added into each filled well, which led to a clear solution or an almost instantaneous precipitation. The result was documented by visual observation and photography against a black background after 1 and 24 h. FIG. 3 shows an exemplary result for (S)-4-Chloro-1-phenylethylamine salts after 1 hour. The procedure was repeated for all amine solutions and the results compared against each other (table 4). The intensity of precipitation, as shown by shade code, serves as a qualitative approximation of salt solubilities and their differences.

TABLE 4 graphical presentation of the screening results

| | exemplary donor amines | | | | | |
|---|---|---|---|---|---|---|
| | isopropyl-amine 3 | | rac-1-phenyl-ethylannine rac-2a | | 2-butyl-amine | LD-alanine |
| conc. | 1000 mM | 250 mM | 1000 mM | 250 mM | each 100 mM | |
| 24CNA | | | SP | | | |
| 25CNA | | | SP | | | |
| 25DHBA | | | | | | |
| 25FDCA | | | | | | |
| 26FBA | | | | | | |
| 2CA | | | | | | |
| 2DPPA | SP | SP | SP | SP | SP | |
| 2FCA | | | | | | |
| 2HNA | | | | | | |
| 2TPCA | | | | | | |
| 32CNA | | | | | | |
| 34CA | | | SP | SP | | |
| 34HHCAA | | | | | | |
| 34NA | | | SP | SP | | |
| 35DNOT | | | SP | SP | | |
| 35HBA | | | | | | |
| 3DPPA | SP | SP | | | SP | |
| 3FCA | | | | | | |
| 3NA | | | SP | | | |
| 42CNA | | | | | | |
| 435CNBA | | | SP | | | |
| 43CNA | | | SP | SP | | |
| 4HBA | | | | | | |
| 43HNBA | | | | | | |
| AA | | | | | | |
| ACC | | | | | | |
| APS | | | | | | |
| ASA | | | | | | |
| BA | | | | | | |
| BCA | | | | | | |
| BPA | | | SP | SP | | |
| BTA | | | | | | |
| BZA | | | | | | |
| CA | | | | | | |
| CCA | | | | | | |
| CHCA | | | SP | | | |
| CMA | | | | | | |
| DBDT | | | | | | |
| DCC | | | | | | |
| DPAA | SP | | SP | SP | | |
| DQA | | | | | | |
| DTA | | | | | | |
| FA | | | | | | |
| FCA | | | | | | |
| FCC | | | | | | |
| GA | | | | | | |
| GCA | | | | | | |
| HA | | | | | | |
| HXCA | | | | | | |

TABLE 4-continued graphical presentation of the screening results

| | | | | | |
|---|---|---|---|---|---|
| INA | | | | | |
| IS | | | | | |
| IVA | | | | | |
| LMA | | | | | |
| LTA | | | | | |
| MA | | | | | |
| NCC | | | | | |
| nNA | | | | | |
| OA | | | | | |
| PA | | | | | |
| PAA | | | | | |
| PCC | | | | | |
| PCPA | | | SP | SP | |
| PFA | | | | | |
| PIA | | | | | |
| PMA | | | | | |
| PPA | | | | | |
| RMA | | | | | |
| SA | | | | | |
| SBCA | | | | | |
| SCA | | | | | |
| SCCA | | | | | |
| SMA | | | | | |
| TG | | | | | |
| TMPA | | | | | |
| TPA | | | | | |
| TPAA | | | | | |
| TPPA | | | | | |
| VA | | | | | |
| VCA | | | | | |
| 24CNA | | | | | |

| | exemplary | exemplary product amines | | | |
|---|---|---|---|---|---|
| conc. | donor amines L-alanine each 100 mM | (S)-1-PEA 2a | (S)-3Cl-1-PEA 2b each 100 mM | (S)-4Cl-1-PEA 2c | (R)-3F-1-PEA 2d |
| 24CNA | | | | | |
| 25CNA | | | | | |
| 25DHBA | | | | | |
| 25FDCA | | | | | |
| 26FBA | | | | | |
| 2CA | | | | | |
| 2DPPA | | SP | | SP | SP |
| 2FCA | | | | | |
| 2HNA | | | | | |
| 2TPCA | | | | | |
| 32CNA | | | | | |
| 34CA | | SP | SP | SP | SP |
| 34HHCAA | | | | | |
| 34NA | | | SP | SP | SP |
| 35DNOT | | SP | SP | | |
| 35HBA | | | | | |
| 3DPPA | | SP | SP | | SP |
| 3FCA | | | | | |
| 3NA | | | SP | | |
| 42CNA | | | | | |

TABLE 4-continued

| graphical presentation of the screening results | | | | |
|---|---|---|---|---|
| 435CNBA | | | | |
| 43CNA | SP | SP | SP | SP |
| 4HBA | | | | |
| 43HNBA | | | | |
| AA | | | | |
| ACC | | | | |
| APS | | | | |
| ASA | | | | |
| BA | | | | |
| BCA | | | | |
| BPA | | | | |
| BTA | | | | |
| BZA | | | SP | |
| CA | | | | |
| CCA | | | | |
| CHCA | | | | |
| CMA | | | | |
| DBDT | | SP | SP | |
| DCC | | | | |
| DPAA | SP | SP | | SP |
| DQA | | | | |
| DTA | | | | |
| FA | | | | |
| FCA | | | | |
| FCC | | | | |
| GA | | | | |
| GCA | | | | |
| HA | | | | |
| HXCA | | | | |
| INA | | | | |
| IS | | | | |
| IVA | | | | |
| LMA | | | | |
| LTA | | | | |
| MA | | | | |
| NCC | | | | |
| nNA | | | | |
| OA | | | | |
| PA | | | | |
| PAA | | | | |
| PCC | | | | |
| PCPA | SP | SP | SP | SP |
| PFA | | | | |
| PIA | | | | |
| PMA | | | | |
| PPA | | | | |
| RMA | | | | |
| SA | | | | |
| SBCA | | | | |
| SCA | | | | |
| SCCA | | | | |
| SMA | | | | |
| TG | | | | |
| TMPA | | | | |
| TPA | | | | |
| TPAA | | | | |

TABLE 4-continued

| graphical presentation of the screening results |
|---|
| TPPA |
| VA |
| VCA |
| 24CNA |

| | exemplary product amines | | |
|---|---|---|---|
| conc. | (R)-4F-<br>1-PEA<br>2e | (S)-3MeO-<br>1-PEA<br>2f<br>each 100 mM | (R)- 4MeO-<br>1-PEA<br>2g |
| 24CNA | \ | SP | |
| 25CNA | | \ | |
| 25DHBA | | | |
| 25FDCA | \ | | |
| 26FBA | | | |
| 2CA | | | |
| 2DPPA | \ | X | SP |
| 2FCA | | | |
| 2HNA | | | |
| 2TPCA | | | |
| 32CNA | | | |
| 34CA | SP | SP | SP |
| 34HHCAA | | | |
| 34NA | X | SP | X |
| 35DNOT | | | |
| 35HBA | | | |
| 3DPPA | SP | SP | X |
| 3FCA | | | |
| 3NA | X | | \ |
| 42CNA | | | |
| 435CNBA | \ | SP | \ |
| 43CNA | X | SP | X |
| 4HBA | | | |
| 43HNBA | | | |
| AA | | | |
| ACC | | | |
| APS | | | |
| ASA | | | |
| BA | SP | \ | \ |
| BCA | | | |
| BPA | | | \ |
| BTA | | | |
| BZA | | | |
| CA | | | |
| CCA | | | |
| CHCA | | | |
| CMA | | | |
| DBDT | | | |
| DCC | | | |
| DPAA | SP | SP | X |
| DQA | | | |
| DTA | SP | | |
| FA | | | |
| FCA | | | |
| FCC | | | |
| GA | | | |
| GCA | | | |
| HA | \ | | |
| HXCA | | | \ |

TABLE 4-continued graphical presentation of the screening results

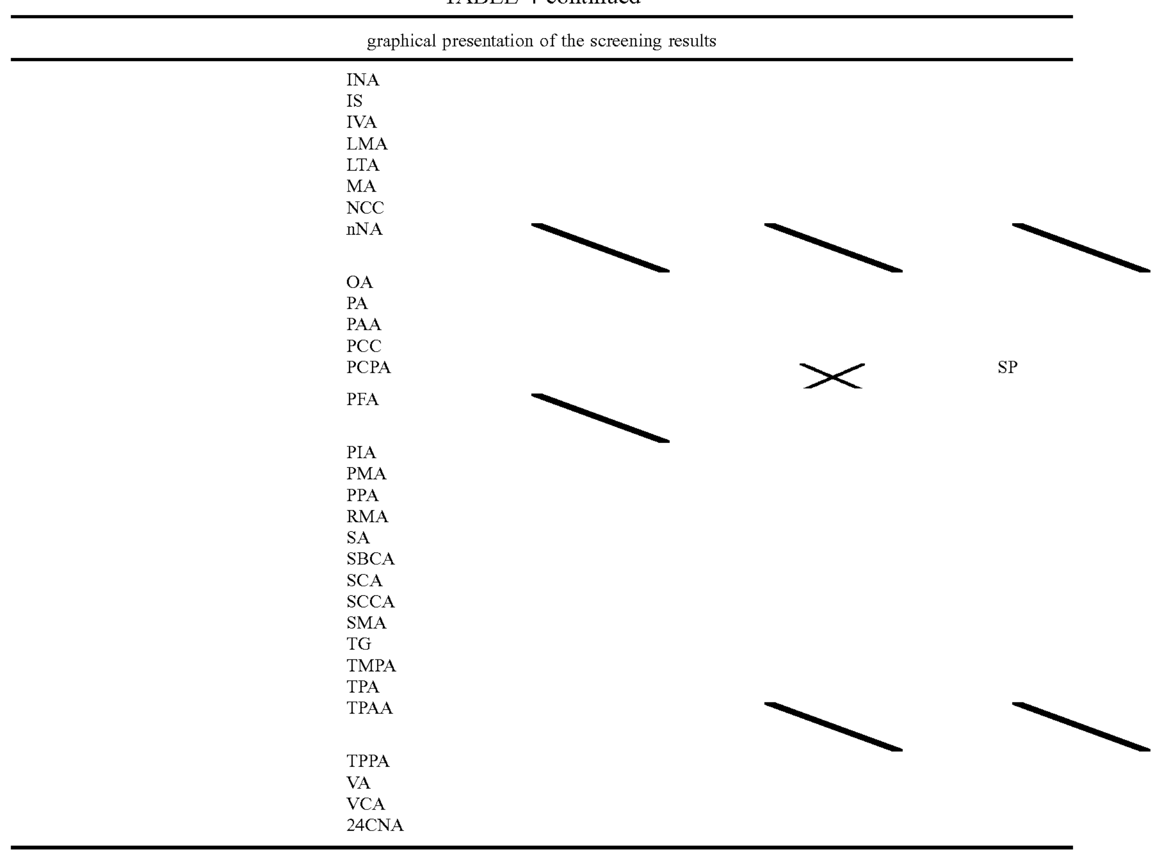

| | | | |
|---|---|---|---|
| INA | | | |
| IS | | | |
| IVA | | | |
| LMA | | | |
| LTA | | | |
| MA | | | |
| NCC | | | |
| nNA | few crystals | few crystals | few crystals |
| OA | | | |
| PA | | | |
| PAA | | | |
| PCC | | | |
| PCPA | | medium precipitation | SP |
| PFA | few crystals | | |
| PIA | | | |
| PMA | | | |
| PPA | | | |
| RMA | | | |
| SA | | | |
| SBCA | | | |
| SCA | | | |
| SCCA | | | |
| SMA | | | |
| TG | | | |
| TMPA | | | |
| TPA | | | |
| TPAA | | few crystals | few crystals |
| TPPA | | | |
| VA | | | |
| VCA | | | |
| 24CNA | | | |

description of symbols and grey shade code for Table 3 no precipitation few crystals medium precipitation

SP significant precipitation

The results of table 3 show clearly that certain acids allow significant differences in solubility between investigated salts. In this screening especially differences between product amines and the commonly used donor amines isopropylamine/alanine were targeted. Based on this consideration the following acids appear most applicable: 34CA, 34NA, 43CNA and 3DPPA. In addition, 2DPPA was identified as suitable acid. Acids with less strong differences are PCPA, 24CNA, 25CNA, 35DNOT, 3NA and 435CNBA, which might be useful for other product amines. PCPA was later excluded from the list of potential acids due to an unknown decomposition reaction of certain salt solutions (strong discoloration).

4. Transaminase-Catalyzed Synthesis of Product Amines in Combination with an In Situ-Product Crystallization General semi-preparative procedure for the amine transaminase-catalyzed synthesis of 2a-k in combination with an in situ-product crystallization of the product amine 6a-k via 3DPPA: To 25 ml 200 mM phosphate buffer pH 7.5 532 μL isopropylamine (≙ 250 mM) and 707 mg 3DPPA (≙ 125 mM) were given and the resulting suspension adjusted to pH 7.5 with aqueous $H_3PO_4$-solution. Afterwards PLP, substrate (≙ 100 mM) and biocatalyst were added and the resulting mixture shaken at 200 rpm. After completion of the reaction the resulting mixture was filtered to obtain the formed product amine salt. (This solid will contain remaining biocatalyst and excess 3DPPA.) Afterwards the solid fraction was washed with 10 mL MTBE to remove remaining substrate and parts of excess 3DPPA. The solid was then given into 5 mL water, 0.5 ml conc. NaOH was added to increase pH and formed product 2 extracted with 5 mL MTBE. After phase separation the product was obtained as its hydrochloride by a slow addition of conc. HCl to the ether phase. 3DPPA can be precipitated from the remaining aqueous solution by adding conc. HCl, e.g. for recycling (isolated yield 71%).

General reaction control procedure: Samples (500 μL) were taken periodically and thoroughly mixed by a vortex mixer with 50 μl conc. NaOH to quench the reaction and increase pH. Afterwards 500 μL MTBE were added, mixed again by a vortex mixer and centrifuged (2 min, 3000 rpm) to improve phase separation. 200 μl were taken from the organic layer, combined with 50 μl of a 25 mM n-decane-solution in MTBE (internal standard) and subsequently analyzed by gas chromatography (column: CP-Chirasil-Dex CB; 25 m, 0.25 mm, 0.25 μm by Agilent, USA)

What is claimed:

1. A method for preparing an amino salt compound, the method comprising:

i) providing a carbonyl compound of general formula (I)

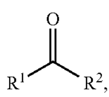

(I)

wherein $R^1$ is selected from the group consisting of branched or unbranched C5-C20-aryl, wherein in case of more than one aromatic ring system the ring systems are condensed or separate, wherein $R^1$ has at least one substituent $R^{1a}$ selected from the group consisting of hydrogen atom, halogen atom, C1-C3-alkyl and C1-C3-alkoxy; and $R^2$ is selected from the group consisting of branched or unbranched C1-C5-alkyl, wherein $R^2$ has at least one substituent $R^{2a}$ selected from the group consisting of hydrogen atom, halogen atom, C1-C3-alkyl and C1-C3-alkoxy;

ii) reacting the carbonyl compound provided according to step (i) in the presence of a transaminase with ii-a) at least one primary amine; and ii-b) at least one carboxylic acid;

thereby obtaining a mixture comprising an at least partially crystallized amino salt compound comprising a cation of general formula (II)

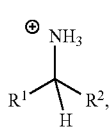

(II)

wherein $R^1$ and $R^2$ are as defined for general formula (I) and a carboxylate anion based on the at least one carboxylic acid added according to (ii-b);

wherein the at least one carboxylic acid according to (ii-b) is a carboxylic acid of general formula (III)

(III)

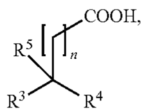

wherein n is zero or 1; the residues $R^3$ and $R^4$ are both phenyl or together form a phenyl ring, wherein a phenyl ring has at least one further substituent selected from the group consisting of hydrogen atom, halogen atom, and nitro group; and the residue $R^5$ is hydrogen atom or methyl or absent if $R^3$ and $R^4$ together form a phenyl ring;

wherein the at least one primary amine according to (ii-a) is selected from the group of mono- and diamines having one to 10 carbon atoms.

2. The method according to claim 1, wherein the amino salt compound obtained according to step (ii) has a solubility in water at pH 7 that is smaller than the solubility in water of the at least one primary amine added according to (ii-a).

3. The method according to claim 2, wherein the transaminase according to step (ii) is selected from the group of amine transaminases.

4. The method according to claim 1, wherein the at least one carboxylic acid according to (ii-b) is a carboxylic acid selected from the group consisting of diphenylacetic acid (DPAA), 2,2-diphenylpropionic acid (2DPPA), 3,3-diphenylpropionic acid (3DPPA), 3,4-dichloro-benzoic acid (34CA), 3,4-dinitro-benzoic acid (34NA) and 4-chloro-3-nitro-benzoic acid (43CNA).

5. The method according to claim 1, wherein the at least one primary amine according to (ii-a) and the at least one carboxylic acid according to (ii-b) are used as one or more salt(s) comprising the protonated form of the at least one primary amine and the deprotonated form of the at least one carboxylic acid.

6. The method according to claim 1, wherein the amino salt compound obtained according to (ii) comprises a cation of general formula (II)

(II)

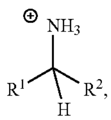

wherein $R^1$ and $R^2$ are as defined for general formula (I), and an anion based on the at least one carboxylic acid, which is an anion of general formula (IIIa)

(IIIa)

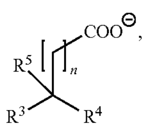

wherein n is zero or 1;

the residues $R^3$ and $R^4$ are both phenyl or together form a phenyl ring, wherein each phenyl ring has at least one further substituent selected from the group consisting of hydrogen atom, halogen atom, and nitro group and the residue $R^5$ is hydrogen atom or methyl or absent if $R^3$ and $R^4$ together form a phenyl ring.

7. The method according to claim 1, further comprising:

iii) separating the at least partially crystallized amine salt compound obtained according to (ii) from the mixture thereby obtaining the crystallized amine salt compound.

8. The method according to claim 2, wherein the amino salt compound obtained according to step (ii) has a solubility in water at pH 7≤30 mmol/l.

9. The method according to claim 1, wherein $R^1$ is phenyl, wherein phenyl has at least one substituent $R^{1a}$ selected from the group consisting of hydrogen atom, halogen atom, and methoxy.

10. The method according to claim 1, wherein the residue $R^2$ is selected from the group of branched or unbranched C1-C3-alkyl.

11. The method according to claim 1, wherein the at least one primary amine according to (ii-a) is selected from the group consisting of 1,5-diamino-pentane (cadaverine), alanine, 2-amino-butane (sec-butylamine) and 2-amino-propane.

* * * * *